(12) United States Patent (10) Patent No.: US 9,073,844 B2
Goossen et al. (45) Date of Patent: Jul. 7, 2015

(54) PROCESS FOR PREPARING A PROPIOLIC ACID OR A DERIVATIVE THEREOF

(75) Inventors: Lukas J. Goossen, Kaiserslautern (DE); Nuria Rodriguez Garrido, Madrid (ES); Filipe Manjolinho Costa, Berlin (DE); Paul P. Lange, Dintikon (CH)

(73) Assignee: BASF SE, Ludwigshafen (DE)

( * ) Notice: Subject to any disclaimer, the term of this patent is extended or adjusted under 35 U.S.C. 154(b) by 116 days.

(21) Appl. No.: 13/816,816

(22) PCT Filed: Aug. 19, 2011

(86) PCT No.: PCT/EP2011/064281
§ 371 (c)(1),
(2), (4) Date: Sep. 26, 2013

(87) PCT Pub. No.: WO2012/022801
PCT Pub. Date: Feb. 23, 2012

(65) Prior Publication Data
US 2014/0012000 A1    Jan. 9, 2014

(30) Foreign Application Priority Data

Aug. 20, 2010 (DE) .......................... 10 2010 034 922

(51) Int. Cl.
| | | |
|---|---|---|
| *C07C 51/15* | (2006.01) | |
| *B01J 31/18* | (2006.01) | |
| *C07D 401/04* | (2006.01) | |
| *C07D 471/04* | (2006.01) | |
| *B01J 31/24* | (2006.01) | |

(52) U.S. Cl.
CPC .............. *C07C 51/15* (2013.01); *B01J 31/183* (2013.01); *C07D 401/04* (2013.01); *C07D 471/04* (2013.01); *B01J 31/2404* (2013.01); *B01J 31/2409* (2013.01)

(58) Field of Classification Search
CPC ............................ C07C 51/15; B01J 31/2409
See application file for complete search history.

(56) References Cited

U.S. PATENT DOCUMENTS

| | | | |
|---|---|---|---|
| 6,342,149 B1 | 1/2002 | Koester et al. | |
| 7,173,149 B2 | 2/2007 | Stohrer et al. | |
| 8,816,127 B2 * | 8/2014 | Zhang et al. .................. | 562/423 |

FOREIGN PATENT DOCUMENTS

| | | |
|---|---|---|
| DE | 198 09 532 | 4/1999 |
| WO | 2011 075087 | 6/2011 |

OTHER PUBLICATIONS

Tsuda et al, Journal of the Chemical Society, Chemical Communications, Carbon Dioxide Insertion into Organocopper and Organosilver Compounds, 1974, pp. 380-381.*
Goossens et al, Advances in Synthetic Catalysis, Synthesis of Propiolic Acids via Copper-Catalyzed Insertion of Carbon Dioxide into the C—H Bond on Terrninal Alkynes, 2010, 352, pp. 2913-2917.*
Arakawa et al,Chemical Reviews, Catalysis Research of Relevance to Carbon Management: Progress, Challenges, and Opportunities, 2001, 701, pp. 953-996.*
Yu, D., et al., "Copper- and copper-N-heterocyclic carbene-catalyzed C—H activating carboxylation of terminal alkynes with CO2 at ambient conditions," PNAS, vol. 107, No. 47, pp. 20184 to 20189, (Nov. 23, 2010).
Gooben, L., et al., "Synthesis of Propiolic Acids via Copper-Catalyzed Insertion of Carbon Dioxide into the C—H Bond of Terminal Alkynes," Adv. Synth. Catal., vol. 352, pp. 2913-2917, (2010).
Wipf, P., et al., "Synthesis of the C1-C11 Segment of Leucascandrolide A," J. Org. Chem, vol. 66, No. 9, pp. 3242-3245, (2001).
Potter, I., et al., "Phosphine displacement reactions by some alkyl-substituted 1,10-phenanthrolines with bis (triphenylphosphine)copper(I)tetrahydroborate," Inorganica Chimica Acta, vol. 207, No. 2, pp. 165-173, (1993).
Crosby, G., et al., "Electronic excited states of copper(I) substituted-1,10-phenanthroline and substituted-phosphine mixed-ligan complexes," Chemical Abstract Services, pp. 1-6, (1989) XP 002665815.
Yersin, H., et al., "Luminescent cyclometalated and chelate metal complexes containing bulky nido-carborane ancillary ligands as components for organic light-emitting devices," Chemical Abstract Service, pp. 1-4, (2009) XP 002665816.
Casadonte, D., Jr., et al., "Hindered internal conversion in rigid media. Thermally nonequilibrated 3IL and 3CT emissions from [Cu(5-X-phen) PPh3)2]+ and [Cu(4, 7-X2-phen) 93PPh3)2]+systems in a glass at 77 K," Chemical Abstract Service, Total 6 Pages, (1987) XP 002665817.
Li, Y., et al., "Structures, electronic states and electroluminescent properties of a series of CuI complexes," Chemical Abstracts Service, pp. 1-2, (2005) XP 002665818.
Sakagami, M., et al., "Pigment sensitized photoelectrochemical cells," Chemical Abstracts Service, pp. 1-2, (Apr. 7, 2000) XP 002665819.
International Search Report Issued Jan. 20, 2012 in PCT/EP11/064281 Filed Aug. 19, 2011.
Kong, Z., et al., "Highly sensitive organic ultraviolet optical sensor based on phosphorescent Cu(I) complex," Chemical Abstracts Service, pp. 1-2, (2006) XP 002665820.
Tsukuda., T., et al., "Luminescence of copper (I) dinuclear complexes bridged by diphosphine ligands," Chemical Abstracts Device, pp. 1-2, (2006) XP 002665821.

(Continued)

*Primary Examiner* — Paul A Zucker
(74) *Attorney, Agent, or Firm* — Oblon, McClelland, Maier & Neustadt, L.L.P.

(57) ABSTRACT

The invention relates to a process for preparing a propiolic acid or a derivative thereof by reacting a terminal alkyne with carbon dioxide, which comprises performing the reaction in the presence of a base and a copper complex, especially a copper (I) complex having at least one ligand, at least one of the ligands of the copper complex being selected from monodentate ligands which have an aminic or iminic nitrogen atom capable of coordination with copper, and polydentate ligands having at least two atoms or atom groups which are capable of simultaneous coordination with copper and are selected from nitrogen, oxygen, sulfur, phosphorus and carbene carbon.

13 Claims, No Drawings

(56) References Cited

OTHER PUBLICATIONS

Sakaki, S., et al., "Successful Photocatalytic Reduction of $MV^{2+}$ with [Cu(NN)(PPh3)2]+(NN=2,9-Dimethyl-1,10-phenanthroline or 4,4',6,6'-Tetramethyl-2,2'-bipyridine)upon Near-UV-Light Irradiation and a Novel Solvent Effect on Its Catalytic Activity," Inorg. Chem., vol. 25, No. 14, pp. 2330-2333, (Jul. 1, 1986).

Trost, B., et al., "Atom Economy. Palladium-Catalyzed Formation of Coumarins by Addition of Phenols and Alkynoates via a Net C—H Insertion," J. Am. Chem. Soc., vol. 125, pp. 4518-4526, (2003).

Kitamura, T., et al., "Transition-Metal-Catalyzed Hydroarylation Reactions of Alkynes Through Direct Functinalitazion of C—H Bonds: A Convinient Tool for Organic Synthesis," Eur. J. Org. Chem., pp. 1111-1125, (2009).

Bararjanian, M., et al., "Six-Component Reactions for the Stereoselective Synthesis of 3-Arylidene-2-oxindoles via Sequential One-Pot Ugi/Heck Carbocyclization/Sonogashira/Nucleophilic Addition," J. Org. Chem., vol. 75, pp. 2806-2812, (2010).

Moon, J., et al., "One-Pot Synthesis of Diarylalkynes Using Palladium-Catalyzed Sonogashira Reaction and Decarboxylative Coupling of sp Carbon and sp2, Carbon," Organic Letters, vol. 10, No. 5, pp. 945-948, (2008).

Moon, J., et al., "Palladium-Catalyzed Decarboxylative Coupling of Alkynyl Carboxylic Acids and Aryl Halides," J. Org. Chem., vol. 74, pp. 1403-1406, (2009).

Jia, W., et al., "Cu-Catalyzed Oxidative Amidation of Propiolic Acids Under Air via Decarboxylative Coupling," Organic Letters, vol. 12, No. 9, pp. 2000-2003, (2010).

Reppe, Von, W., et al., "Athnylierung," Justus Liebigs Annalen Der Chemie, pp. 1-4, (Apr. 10, 1955).

Mizuno, T., et al., "Carbonylation of aryl and alkyl halides catalyzed by a binuclear rhodium hydroxide complex," Journal of Molecular Catalysis A: Chemical, vol. 123, pp. 21-24, (1997).

Arzoumanian, H., et al., "Mono- and Dicarboxylation of α-Haloalkynes Catalyzed by Nickel Cyanide under Phase-Transfer Conditions," Organometallics, vol. 11, pp. 493-495, (1992).

Tsuji, J., et al., "Facile Synthesis of Acetylenecarboxylates by the Oxidative Carbonylation of Terminal Acetylenes Catalyzed by PdCl2 Under Mild Conditions," Tetrahedron Letters, vol. 21, pp. 849-850, (1980).

Jones, E.R.H., et al., "Researches on Acetylenic Compounds. Part LVII A General Synthesis of Allenic Acids," J. Chem. Soc., pp. 4628 to 4633, (Jan. 1, 1957).

Satyanarayana, N., et al., "Stereoselective Synthesis of Diacids by the Nickel Cyanide and Phase-Transfer-Catalyzed Carbonylation of Alkynols. Novel Dependency of Product Stereochemistry and Optimum Stirring Speed on the Nature of the Phase-Transfer Agent," Organometallics, vol. 10, No. 3, pp. 804-807, (1991).

Li, J., et al., "Palladium Catalyzed Carbonylation of Terminal Acetylenes: A New Method for Synthesis of Acetylenecarboxylates," Synthetic Communications, vol. 31(2), pp. 199-202, (2001).

Izawa, Y., et al., "Palladium-Catalyzed Oxidative Carbonylation of 1-Alkynes into 2-Alkynoates with Molecular Oxygen as Oxidant," Bull. Chem. Soc. Jpn., vol. 77, pp. 2033-2045, (2004).

Kollar, L., "Modern Carbonylation Methods," Recent Developments in Alkyne Carbonylationk, Recent Developments in Alkyne Carbonylation, Total 8 Pages, (2008).

Sakakura, T., et al., "The synthesis of organic carbonates from carbon dioxide," ChemComm, pp. 1312-1330, (2009).

Sakakura, T., et al., "Transformation of Carbon Dioxide," Chem. Rev., vol. 107, pp. 2365-2387, (2007).

Eghbali, N., et al., "Conversion of carbon dioxide and olefins into cyclic carbonates in water," Green Chemistry, vol. 9, pp. 213-215, (2007).

Arakawa, H., et al., "Catalysis Research of Relevance to Carbon Management: Progres, Challenges, and Opportunities," Chem. Rev., vol. 101, pp. 953-996, (2001).

Voss, S., et al., "Ueber Propiolsaeure und Propiolsaeure-anhydrid," Propiolsaeure v. Propiolsaeure-anhydrid, pp. 1681-1691, (1926).

Sonogashira, K., "Palladium-Catalyzed Alkynylation," Handbook of Organopalladium Chemistry for Organic Synthesis, pp. 493-529, (2004).

Boyall, D., et al., "Efficient Enantioselective Additions of Terminal Aklynes and Aldehydes under Operationally Convenient Conditions," Organic Letters, vol. 4, No. 15, pp. 2605-2606, (2002).

Tsuda, T, et al., "Carbon Dioxide Insertion into Organocopper and Organosilver Compounds," J.C.S. Chem. Comm., pp. 380-381, (1974).

Tsuda, T., et al., "Reversible Carbon Dioxide Fixation by Organocopper Complexes," J.C.S. Chem. Comm., pp. 963-964, (1975).

Fukue, Y., et al., Direct Synthesis of Alkyl 2-Alkynoates from Alk-1-ynes, CO2, and Bromoalkanes Catalysed by Copper(I) or Silver(I) Salt, J. Chem. Soc., Chem. Commun., p. 2091, (1994).

Boogaerts, I.F., et al., "Carboxylation of C—H Bonds Using N-Heterocyclic Carbene Gold(I) Complexes," JACS Communications, pp. 8858-8859, vol. 132, (2010).

Goossen, L., et al., "Copper-Catalyzed Protodecarboxylation of Aromatic Carboxylic Acids," Adv. Synth. Catal., vol. 349, pp. 2241-2246, (2007).

Goossen, L., et al.,"Microwave-Assisted Cu-Catalyzed Protodecarboxylation of Aromatic Caboxylic Avids," vol. 74, pp. 2620-2623, (2009).

Goossen, L., et al., "Comparative Study of Copper- and Silver-Catalyzed Protodecarboxylations of Carboxylic Acids," ChemCatChem, vol. 2, pp. 430-442, (2010).

* cited by examiner

PROCESS FOR PREPARING A PROPIOLIC ACID OR A DERIVATIVE THEREOF

The invention relates to a process for preparing propiolic acids by reacting terminal alkynes with carbon dioxide in the presence of a transition metal catalyst.

Propiolic acids are versatile synthetic building blocks, e.g. in cycloadditions or hydroarylation reactions. Propiolic acids make it possible to synthesize many heterocyclic compounds such as coumarins, flavones and indoles (see, for example, a) B. M. Trost, F. D. Toste, K. Greenman, *J. Am. Chem. Soc.* 2003, 125, 4518-4526; b) T. Kitamura, *Eur. J. Org. Chem.* 2009, 1111-1125; c) M. Bararjanian, S. Balalaie, F. Rominger, B. Movassagh, H. R. Bijanzadeh, *J. Org. Chem.* 2010, 75, 2806-2812.). In addition, they are used in decarboxylating cross-couplings for the synthesis of alkynylarenes or aminoalkynes (a) J. Moon, M. Jeong, H. Nam, J. Ju, J. H. Moon, H. M. Jung, S. Lee, *Org. Lett.* 2008, 10, 945-948; b) J. Moon, M. Jang, S. Lee, *J. Org. Chem.* 2009, 74, 1403-1406; c) W. Jia, N. Jiao, *Org. Lett.* 2010, 12, 2000-2003.).

The synthesis of propiolic acids traditionally requires multistage processes such as the addition of alkynes onto formaldehyde and the subsequent oxidation of the resulting propargyl alcohol (see, for example, a) W. Reppe, *Liebigs Ann. Chem.* 1955, 596, 1-4; b) J. Stohrer, E. Fritz-Langhals, C. Brüninghaus, U.S. Pat. No. 7,173,149B2, 2007), the carbonylation of unstable alkynyl halogen compounds which are difficult to obtain commercially (see, for example, a) T. Mizuno, H. Alper, *Journal of Molecular Catalysis A: Chemical* 1997, 123, 1-24; b) H. Arzoumanian, F. Cochini, D. Nuel, J. F. Petrignani, N. Rosas, *Organometallics* 1992, 11, 493-495) or the lithiation of terminal alkynes and subsequent reaction with chloroformate (see, for example, a) J. Tsuji, M. Takahashi, and T. Takahashi, *Tetrahedron Lett.* 1980, 21, 849; b) E. R. H. Jones, G. H. Whitham, M. C. Whiting, *J. Chem. Soc.* 1957, 4628-4633; c) N. Satyanarayana, H. Alper, *Organometallics* 1991, 10, 804-807; d) J. Li, H. Jiang, M. Chen, *Synth. Commun.* 2001, 31, 199-202; e) Y. Izawa, I. Shimizu, A. Yamamoto, *Bull. Chem. Soc. Jpn.* 2004, 77, 2033-2045; f) L. Kollár, *Modern Carbonylation Reactions*, Wiley-VCH, Weinheim, 2008, pp. 276-280.). In addition, there are processes for the oxidative carbonylation of alkynes by means of carbon monoxide.

The disadvantages of all these access routes result from the choice of the C1 building blocks: formaldehyde and chloroformate are toxic and comparatively expensive, and carbon monoxide is a toxic gas which is difficult to handle.

Carbon dioxide is from many points of view an attractive C1 building block for forming the carboxylate unit (a) T. Sakakura, K. Kohon, *Chem. Commun.* 2009, 1312-1330; b) T. Sakakura, J.-C. Choi, H. Yasuda, *Chem. Rev.* 2007, 107, 2365-2387; c) N. Eghbali, C.-J. Li, *Green Chem.* 2007, 9, 213-215; d) H. Arakawa, et al., *Chem. Rev.* 2001, 101, 953-996.). It is available inexpensively in large quantities as waste product from many combustion processes and is easy to handle. The utilization of carbon dioxide as raw material is also ecologically advantageous since it counters the greenhouse effect caused by $CO_2$.

However, the synthesis of propiolic acids from carbon dioxide has hitherto only succeeded when using expensive metal-organic reagents, for example alkynylmagnesium, alkynylzinc or alkynyllithium reagents (L. Brandsma, *Preparative Acetylenic Chemistry*, 2$^{nd}$ Ed., Elsevier, Amsterdam, 1998.). The carboxylation using such expensive compounds whose synthesis requires a strong metal basis is economically disadvantageous.

The synthesis of propiolic acids from carbon dioxide can be successfully carried out starting from sodium acetylide (Strauss, Voss, *Ber df chem. Ges.* 1926, p. 1681-1691). Sodium acetylide can be produced only by means of extremely strong bases such as sodium hydride or metallic sodium. The presence of oxygen-comprising bases such as sodium hydroxide leads to carbonization or spontaneous ignition of the reaction mixture, which can be avoided only by mixing with large amounts of sand. The reaction of sodium acetylide with carbon dioxide under the conditions reported by Strauss et al. is extremely slow; only after three weeks were satisfactory conversions observed. Such slow reactions are unsuitable for industrial applications.

The optimal strategy both from an economic and an ecological point of view would be a single-stage catalytic carboxylation of terminal alkynes by means of carbon dioxide with C—H functionalization to form the corresponding alkyne carboxylic acids. There was therefore a need for a process which allows the reaction of terminal alkynes with carbon dioxide in the presence of weak bases.

Coupling reactions of alkynes with rupture of C—H bonds in the presence of only weak bases, i.e. compounds whose basicity is not sufficient to deprotonate a terminal alkyne in the absence of a catalyst, are known for palladium/copper-aided cross-couplings with aryl halides (Sonogashira reaction) (K. Sonogashira, E.-I. Negishi, Eds. *Handbook of Organopalladium Chemistry for Organic Synthesis*, Wiley-VCH: New York, 2004; pp 493-529.) or transition metal-aided 1,2-additions of alkynes (D. Boyall, D. E. Frantz, E. M. Carreira, *Org. Lett* 2002, 4, 2605-2606.). However, there has hitherto not been any example of a process by means of which terminal alkynes can be deprotonated by means of a weak base in the presence of a transition metal and be reacted in high yields with carbon dioxide directly in the reaction mixture to form the propiolic acids. The reason is that known carboxylation catalysts require relatively high temperatures. However, the propiolic acid products which can be obtained by carboxylation of alkynes by means of carbon dioxide in the presence of copper salts are so thermally unstable that they immediately decompose again into the alkyne starting materials with elimination of carbon dioxide as soon as the supply of carbon dioxide is stopped (T. Tsuda, K. Ueda, T. Saegusa, *J. C. S. Chem. Comm.* 1974, 380-381.).

Saegusa et al. showed that simple copper salts allow the reversible fixing of carbon dioxide. However, owing to the reversibility of the reaction, they were not able to isolate the propiolic acids formed in equilibrium (T. Tsuda, K. Ueda, T. Saegusa, *J. C. S. Chem. Comm.* 1975, 963-964.). Only when they added an alkylating agent, i.e. 1-bromohexane, and thus continuously removed the carboxylic acids as esters from the equilibrium were they able to achieve satisfactory conversions (Y. Fukue, S, Oi, Y. Inoue, *J. C. S. Chem. Comm.* 1994, 2091.). However, the use of halogen compounds makes the overall process disadvantageous, especially when it is not the propiolic esters but the propiolic acids which are the desired target compounds.

This reversibility of the insertion of carbon dioxide is a general problem in carboxylation reactions. Nolan et al., briefly reported the carboxylation of C═H acid heterocycles in the presence of gold catalysts (I. I. F. Boogaerts, S. P. Nolan, *J. Am. Chem. Soc.* 2010, 132, 8858-8859.). In this case, too, the resulting carboxylic acids were isolated predominantly in the form of the corresponding esters.

In contrast to the reaction of acetylenes with carbon dioxide, the above-described reaction of metal acetylides with carbon dioxide in the absence of any proton source is irreversible. However, a prerequisite for this is that the conditions are so basic that no acetylene but only a metal acetylide was able to be formed.

It is an object of the present invention to provide a process which makes it possible to prepare propiolic acids in sensible yields and with an economically justifiable outlay by reacting corresponding terminal alkynes with $CO_2$. In particular, the process should ensure that the equilibrium of the enthalpically advantageous but entropically unfavorable carboxylation of alkynes can be shifted far to the side of the propiolic acids. The process should make it possible for propiolic acids to be prepared in good yields from alkynes and carbon dioxide and be isolated without decomposition.

These and further objects are achieved by the process defined in the claims and explained in more detail below.

The invention provides a process for preparing a propiolic acid or a derivative thereof by reacting a terminal alkyne with carbon dioxide, wherein the reaction is carried out in the presence of a base and a copper complex, in particular a copper(I) complex, which has at least one ligand, where at least one of the ligands of the copper complex is selected from among monodentate ligands which have an amine or imine nitrogen atom which is capable of coordinating to copper and polydentate ligands which have at least two atoms or atom groups which are capable of coordinating simultaneously to copper and are selected from among nitrogen, oxygen, sulfur, phosphorus and carbene carbon.

The invention relates in particular to a process for preparing a propiolic acid or a derivative thereof by reacting a terminal alkyne with carbon dioxide, wherein the reaction is carried out in the presence of a base and a copper complex having at least one polydentate nitrogen ligand which has at least two atoms or atom groups which are capable of coordinating to copper and are selected from among nitrogen, oxygen, sulfur, phosphorus and carbene carbon.

The copper complexes used according to the invention reduce the activation barrier for the insertion of carbon dioxide into the acetylenic C—H bond of the terminal alkyne to such an extent that the carboxylation/decarboxylation equilibrium is virtually completely on the side of the carboxylated products, i.e. the propiolic acids, even at low partial pressures of carbon dioxide. That this succeeded in such a high efficiency is surprising since such copper catalysts also readily catalyze the undesirable backreaction, viz. the decarboxylation reaction (a) L. J. Gooßen, W. R. Thiel, N. Rodríguez, C. Linder, B. Melzer, *Adv. Synth. Catal.* 2007, 349, 2241-2246; b) L. J. Gooßen, F. Manjolinho, B. A. Khan, N. Rodríguez, *J. Org. Chem.* 2009, 74, 2620-2623; c) L. J. Gooßen, N. Rodríguez, C. Linder, P. P. Lange, A. Fromm, *Chem Cat Chem* 2010, 2, 430-442.).

For the purposes of the present invention, "terminal alkynes" are compounds having at least one —C≡C—H group.

The terminal alkynes have, for example, the general formula X

where $R^x$ is hydrogen, $COOR^{x1}$, alkyl, alkenyl, cycloalkyl, heterocycloalkyl, aryl, hetaryl or $(R^{x2})_3Si$ and alkyl and alkenyl are unsubstituted or have one or more substituents, e.g. 1, 2, 3, 4 or 5 substituents $R^{x3}$ and cycloalkyl, heterocycloalkyl, aryl and hetaryl are unsubstituted or substituted by one or more substituents, e.g. 1, 2, 3, 4 or 5 substituents $R^{x4}$, where $R^{x1}$ is selected from among hydrogen, alkyl, cycloalkyl, heterocycloalkyl, aryl and hetaryl, where the latter four radicals are unsubstituted or have one or more, e.g. 1, 2 or 3, radicals selected from among hydroxy (=OH), mercapto (=SH), $NE^1E^2$, $C(O)NE^1E^2$, halogen, nitro (=$NO_2$), nitroso (=NO), formyl (=C(=O)H), alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl and cycloalkyl, $R^{x2}$ is selected from among alkyl, cycloalkyl, heterocycloalkyl, aryl and hetaryl, where the latter four radicals are unsubstituted or have one or more, e.g. 1, 2 or 3, radicals selected from among hydroxy, mercapto, $NE^1E^2$, $C(O)NE^1E^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl and cycloalkyl, $R^{x3}$ is selected from among halogen, cyano, hydroxy, mercapto, alkoxy, COOH, $SO_3H$, $NE^1E^2$, $C(O)NE^1E^2$, acyl, alkoxycarbonyl, cycloalkyl, heterocycloalkyl, aryl, hetaryl, cycloalkoxy, heterocycloalkoxy, aryloxy, hetaryloxy, cycloalkoxycarbonyl, heterocycloalkoxycarbonyl, aryloxycarbonyl and hetaryloxycarbonyl, where the cyclic groups in the latter twelve radicals are unsubstituted or have one or more, e.g. 1, 2 or 3, radicals selected from among hydroxy, mercapto, $NE^1E^2$, $C(O)NE^1E^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl and cycloalkyl, $R^{x4}$ is selected from among halogen, cyano, nitro, hydroxy, mercapto, alkoxy, COOH, $SO_3H$, $NE^1E^2$, $C(O)NE^1E^2$, alkyl, haloalkyl, acyl, alkoxycarbonyl, cycloalkyl, heterocycloalkyl, aryl, hetaryl, cycloalkoxy, heterocycloalkoxy, aryloxy, hetaryloxy, cycloalkoxycarbonyl, heterocycloalkoxycarbonyl, aryloxycarbonyl and hetaryloxycarbonyl, where the cyclic groups in the latter twelve radicals are unsubstituted or have one or more, e.g. 1, 2 or 3, radicals selected from among hydroxy, mercapto, $NE^1E^2$, $C(O)NE^1E^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl and cycloalkyl, where $E^1$ and $E^2$ are identical or different radicals selected from among hydrogen, alkyl, cycloalkyl and aryl or $E^1$ and $E^2$ together with the nitrogen atom to which they are bound form a saturated nitrogen heterocyclyl which is unsubstituted or has one or more alkyl groups as substituents.

The propiolic acids obtained in the process of the invention have, for example, the general formula XI

where $R^x$ has the meanings given above for formula X and in particular the meanings mentioned below. If acetylene is used as terminal alkyne ($R^x$=H), acetylene dicarboxylic acid can also be prepared, depending on the reaction conditions.

In the process of the invention, preference is given to reacting terminal alkynes of the formula X in which $R^x$ is hydrogen, alkyl, cycloalkyl or phenyl, where alkyl is unsubstituted or bears 1 or 2 radicals $R^{x3}$ which are preferably selected from among alkoxy, cycloalkyl and phenyl and phenyl and cycloalkyl are unsubstituted or bear 1, 2 or 3 radicals $R^{x4}$ which are preferably selected from among hydroxy, mercapto, $NE^1E^2$, $C(O)NE^1E^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl and cycloalkyl. In a particularly preferred embodiment of the invention, acetylene, i.e. a terminal alkyne in which $R^x$ is hydrogen, is used as terminal alkyne.

Here and in the following, the terms halogen, alkyl, haloalkyl, alkoxy, haloalkoxy, alkylthio, haloalkylthio, alkylcarbonyl, alkylcarbonyloxy, alkylcarbonylthio, haloalkylcarbonyl, acyl, alkoxycarbonyl, cycloalkyl, heterocycloalkyl, aryl, hetaryl, cycloalkoxy, heterocycloalkoxy, aryloxy, hetaryloxy, arylthio, hetarylthio, cycloalkoxycarbonyl, heterocycloalkoxycarbonyl, aryloxycarbonyl and hetaryloxycarbonyl mentioned in connection with the substituents are collective terms for groups of substituents. In connection with the substituents, the prefix $C_n$-$C_m$ indicates the range for the possible number of carbon atoms which such a substituent can have in each case.

Halogen is fluorine, chlorine, bromine and iodine, preferably fluorine, chlorine and bromine.

The expression "alkyl" comprises straight-chain and branched alkyl groups generally having from 1 to 20 carbon atoms ($C_1$-$C_{20}$-alkyl), frequently from 1 to 12 carbon atoms ($C_1$-$C_{12}$-alkyl) and in particular from 1 to 8 carbon atoms ($C_1$-$C_8$-alkyl). Preference is given to straight-chain or branched $C_1$-$C_{12}$-alkyl groups and particularly preferably $C_1$-$C_8$-alkyl groups or $C_1$-$C_4$-alkyl groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl and decyl.

The expression "haloalkyl" comprises straight-chain and branched alkyl groups generally having from 1 to 20 carbon atoms ($C_1$-$C_{20}$-haloalkyl), frequently from 1 to 12 carbon atoms ($C_1$-$C_{12}$-haloalkyl) and in particular from 1 to 8 carbon atoms ($C_1$-$C_8$-haloalkyl) or from 1 to 4 carbon atoms ($C_1$-$C_8$-haloalkyl), where at least one, e.g. 1, 2, 3, 4 or 5, of the hydrogen atoms have been replaced by halogen atoms, in particular by fluorine atoms. Examples of haloalkyl groups are fluoromethyl, difluoromethyl, trifluoromethyl, 1-fluoroethyl, 2-fluoroethyl, 1,1-difluoroethyl, 2,2-difluoroethyl, 1,2-difluoroethyl, 2,2,2-trifluoroethyl, 1,1,2,2-tetrafluoroethyl, pentafluoroethyl, 1-fluoropropyl, 2-fluoropropyl, 3-fluoropropyl, 2,3-difluoropropyl, 1,1-difluoropropyl, 1,2-difluoropropyl, 2,2-difluoropropyl, 3,3-difluoropropyl, 3,3,3-trifluoropropyl, 2,2,3,3,3-pentafluoropropyl, heptafluoropropyl, 2-fluoro-2-propyl, 1-fluoro-2-propyl, 1,1-difluoro-2-propyl, 1,1,1-trifluoro-2-propyl and heptafluoro-2-propyl.

The expression "alkenyl" comprises straight-chain and branched hydrocarbon groups having at least one ethylenic unsaturation. Preference is given to straight-chain or branched $C_2$-$C_{20}$-alkenyl groups, preferably $C_2$-$C_{12}$-alkenyl groups, particularly preferably $C_2$-$C_8$-alkenyl groups.

The expression "cycloalkyl" preferably comprises $C_5$-$C_7$-cycloalkyl groups such as cyclopentyl, cyclohexyl or cycloheptyl.

The expression "heterocycloalkyl" comprises saturated, cycloaliphatic groups which generally have from 4 to 7, preferably 5 or 6, ring atoms and in which 1, 2, 3 or 4 of the ring carbons have been replaced by heteroatoms, preferably selected from among the elements oxygen, nitrogen and sulfur, and may optionally be substituted. Examples of such heterocycloaliphatic groups are pyrrolidinyl, piperidinyl, 2,2,6,6-tetramethylpiperidinyl, imidazolidinyl, pyrazolidinyl, oxazolidinyl, morpholinyl, thiazolidinyl, isothiazolidinyl, isoxazolidinyl, piperazinyl, tetrahydrothiophenyl, tetrahydrofuranyl, tetrahydropyranyl, dioxanyl.

The expression "aryl" preferably comprises $C_6$-$C_{14}$-aryl groups, preferably phenyl, tolyl, xylyl, mesityl, naphthyl, fluorenyl, anthracenyl, phenanthrenyl or naphthacenyl, particularly preferably phenyl or naphthyl.

The expression "hetaryl" comprises heterocycloaromatic groups which are made up of one or two or three fused 5- or 6-membered aromatic rings, where 1, 2, 3 or 4 of the ring carbons in at least one ring have been replaced by a heteroatom, preferably selected from among the elements oxygen, nitrogen and sulfur, preferably the groups pyridyl, quinolinyl, acridinyl, pyridazinyl, pyrimidinyl, pyrazinyl, triazinyl, tetrazinyl, pyrrolyl, pyrazolyl, isoxazolyl, imidazolyl, oxazolyl, thiazolyl, thiophenyl, furanyl.

The above explanations regarding the expressions "alkyl", "haloalkyl", "cycloalkyl", "aryl", "heterocycloalkyl" and "hetaryl" apply analogously to the expressions "alkoxy", "haloalkoxy", "alkylthio", "haloalkylthio", "alkylcarbonyl", "alkylcarbonyloxy", "haloalkylcarbonyl", "haloalkylcarbonyloxy", "aryloxy", "arylthio", "hetaryloxy", "heterocycloalkoxy", "hetarylthio", "alkoxy(carbonyl)", "cycloalkoxy(carbonyl)", "aryloxy(carbonyl)", "heterocycloalkoxy(carbonyl)" and "hetaryloxy(carbonyl)". Here, "alkoxy" is an alkyl radical as defined above bound via an oxygen atom. "Haloalkoxy", "cycloalkoxy", "heterocycloalkoxy", "aryloxy" and "hetaryloxy" correspondingly each refer to a haloalkyl, cycloalkyl, heterocycloalkyl, aryl and hetaryl group, respectively, bound via an oxygen atom. "Alkylthio" is an alkyl radical as defined above bound via a sulfur atom. "Haloalkylthio", "cycloalkylthio", "heterocycloalkylthio", "arylylthio" and "hetarylylthio" correspondingly each refer to a haloalkyl, cycloalkyl, heterocycloalkyl, aryl and hetaryl group, respectively, bound via a sulfur atom.

For the purposes of the present invention, the expression "acyl" refers to the formyl group or alkanoyl or aroyl groups generally having from 2 to 11, preferably from 2 to 8, carbon atoms, for example the acetyl, propanoyl, butanoyl, pentanoyl, hexanoyl, heptanoyl, 2-ethylhexanoyl, 2-propylheptanoyl, benzoyl or naphthoyl group.

The group $NE^1E^2$ is preferably N,N-dimethylamino, N,N-diethylamino, N,N-dipropylamino, N-methyl-N-ethylamino, N-methyl-N-propylamino, N-methyl-N-isopropylamino, N-methyl-N-butylamino, N-methyl-N-tert-butylamino, N-methyl-N-cyclohexylamino, N-methyl-N-phenylamino, N,N-diisopropylamino, N,N-di-n-butylamino, N,N-di-tert-butylamino, N,N-dicyclohexylamino, N,N-diphenylamino, 4-morpholinyl, 1-piperidinyl, 1-pyrrolidinyl or 4-methyl-1-piperazinyl.

Fused ring systems can be aromatic, hydroaromatic and cyclic compounds joined by fusion (fused-on). Fused ring systems comprise two, three or more than three rings. Depending on the type of linkage, a distinction is made among fused ring systems between ortho-fusion, i.e. each ring shares an edge or two atoms with each adjacent ring, and peri-fusion in which a carbon atom belongs to more than two rings. Among the fused ring systems, preference is given to ortho-fused ring systems.

In the process of the invention, terminal alkynes are reacted with carbon dioxide according to the general Scheme 1 in the presence of copper complexes and bases to form propiolic acids or derivatives thereof. Derivatives are, in particular, metal salts and esters of the propiolic acids. The reaction is preferably carried out in such a way that the free propiolic acid is obtained after work-up.

Scheme 1:

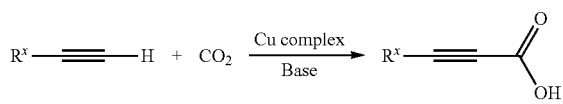

In the case of $R^x$=H, i.e. when acetylene is used as substrate, carboxylation can, according to Scheme 2, be carried out as a matter of choice at only one end or at both ends, then forming the acetylenedicarboxylic acid. This reaction, which is also illustrated in example 41, is particularly surprising since acetylene is known to form stable complexes with copper salts and its reactivity toward transition metals often differs significantly from that of its longer-chain derivatives.

Scheme 2:

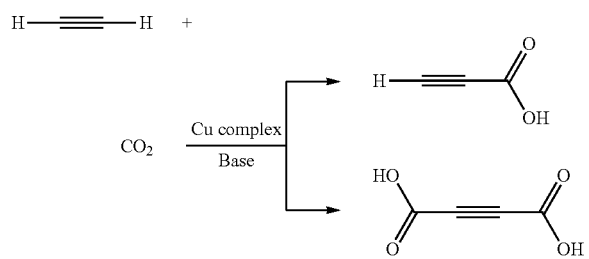

In a first embodiment of the process of the invention, copper complexes, in particular copper(I) complexes, in which at least one of the ligands of the copper complex is selected from among monodentate ligands which have an amine or imine nitrogen atom which is capable of coordinating to copper serve as catalysts. Examples of monodentate ligands having amine nitrogen atoms are, in particular, tertiary aliphatic and cycloaliphatic amines which have a tertiary amino group. Examples of ligands which have an imine nitrogen atom are pyridine, pyridines substituted by one or more $C_1$-$C_4$-alkyl groups and also imidazole and N—$C_1$-$C_4$-alkylimidazoles.

In a preferred embodiment of the process of the invention, copper complexes, in particular copper(I) complexes, having at least one polydentate ligand serve as catalysts. The copper complexes used according to the invention are generally chelate complexes of the polydentate ligand with the copper atom, which optionally bears one or more further ligands.

For the purposes of the present invention, a "polydentate ligand" is a compound which can simultaneously form a coordinate bond to the copper atom simultaneously via at least two donor atoms or donor atom groups. Such donor atoms can be heteroatoms such as sulfur, oxygen or nitrogen. Examples of phosphorus atoms which can function as donor atoms are "trivalent" phosphorus atoms which are present in the form of phosphine groups or phosphonite groups in the ligand. Examples of sulfur atoms which can function as donor atoms are, in particular, monovalent and divalent sulfur atoms which are, for example, present as mercaptan groups, as thioether group, as thiocarbonyl groups or as thioisocyanate groups in the ligand. Examples of oxygen atoms which can function as donor atoms are, in particular, monovalent and divalent oxygen atoms which are, for example, present as hydroxyl groups, as carbonyl groups, carboxylate groups or as oxime groups in the ligand. Examples of nitrogen atoms which can function as donor atoms are, in particular, monovalent, divalent or trivalent nitrogen atoms which are, for example, present as primary, secondary or tertiary amino groups, as hydroxylamino groups, as imino groups, including oxime groups, or as nitrene groups in the ligand. The donor atom can also be a carbon atom present as divalent carbon, i.e. as carbon bound in a carbenoid fashion (carbene carbon), in the ligand. Preferred polydentate ligands are, in particular, those which have at least one nitrogen atom and in particular at least two nitrogen atoms as donor atom(s).

In the process of the invention, preference is given to using copper complexes, in particular copper(I) complexes, having at least one polydentate nitrogen ligand which has at least two nitrogen atoms which are capable of coordinating to copper atoms as catalysts. The copper complexes having a polydentate nitrogen ligand which are preferably used according to the invention are generally chelate complexes of the polydentate nitrogen ligand with the copper atom which optionally bears one or more further ligands.

For the purposes of the present invention, a "polydentate nitrogen ligand" is a compound which can form a coordinate bond to the copper atom via at least two nitrogen donor atoms. Preference is given to bidentate nitrogen ligands, i.e. ligands which have precisely two nitrogen donor atoms which can in each case form a coordinate bond to the copper atom. Such ligands will hereinafter also be referred to as (N,N)-ligand. In these ligands, the nitrogen is preferably present in the form of an alkylamine, cycloalkylamine, heterocycloalkylamine, arylamine, heteroarylamine, alkylimine, cycloalkyllimine, heterocycloalkylimine, arylimine or heteroarylimine group, in particular in the form of a heterocyclylimine or heteroarylimine group, where the imino group is a constituent of the heterocyclylimine or heteroarylimine group, e.g. in the form of a heteroarylimine group selected from among pyridine, pyrimidine, pyrazine, pyridazine, pyrrole, 1H-indole, imidazole, oxazole, thiazole and pyrazole groups, or in the form of a heterocycloalkylimine group selected from among 3,4,5,6-tetrahydropyridine, 1,2,5,6-tetrahydropyrimidine, 1,4,5,6-tetrahydropyrimidine, 1,2,3,6-tetrahydropyrazine, 3,4,5,6-tetrahydropyridazine, pyrroline, 3H-indole, imidazoline, oxazoline, thiazoline and 4,5-dihydropyrazole groups. The abovementioned cyclic groups are in turn unsubstituted or have one or more, e.g. 1, 2, 3 or 4, of the substituents $R^s$ described in more detail below.

The copper complex can bear further ligands in addition to the polydentate nitrogen ligand. All ligands are preferably uncharged.

Preference is given to using copper(I) complexes, i.e. copper is present in the oxidation state +I. The counterion required to achieve electrical neutrality is any anion selected, for example, from among halides such as I$^-$, Br$^-$, Cl$^-$, F$^-$, (hydrogen)carbonate [HCO$_3^-$, CO$_3^{2-}$], (hydrogen)phosphates [PO$_4^{3-}$, HPO$_4^{2-}$, H$_2$PO$_4^-$], carboxylates such as formate, acetate, propionate, benzoate; hydroxide [OH$^-$], oxide [O$^{2-}$], alkoxides such as methoxide, ethoxide; phenoxides, nitrate [NO$_3^-$], (hydrogen)sulfate [SO$_4^-$, HSO$_4^-$], complex anions such as BF$_4^-$, PF$_6^-$, AsF$_6^-$, SbF$_6^-$, BPh$_4^-$; sulfonates such as tosylate, trifluoromethanesulfonate and methylsulfonate.

The polydentate nitrogen ligand preferably has a skeleton having the formula I,

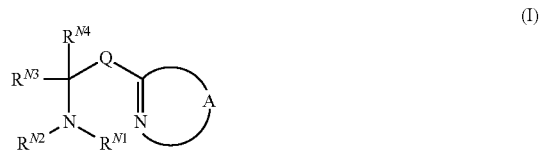

(I)

where
A together with the fragment C=N to which it is bound forms a 5- to 7-membered heterocyclic ring, in particular a 5- or 6-membered heteroaromatic ring, which may be fused with one, two or three further rings;
Q is a chemical bond or a bridging group having one, two or three atoms, where the chemical bond or bridging group can in part or in its entirety be a constituent of one or more rings, where in the case of a cyclic group Q this can be fused with the ring A;
$R^{N1}$ is hydrogen or
$R^{N1}$ together with $R^{N4}$ forms a chemical bond,
$R^{N2}$ is alkyl, cycloalkyl or aryl
$R^{N3}$ is hydrogen, alkyl, cycloalkyl or aryl, where alkyl is unsubstituted or bears a radical selected from the group consisting of cycloalkyl or aryl;
$R^{N2}$ and $R^{N3}$ together with the atoms to which they are bound form a 5- to 7-membered heterocyclic ring, in particular a 5- or 6-membered heteroaromatic ring, which may be fused with one, two or three further rings, in particular a cyclic group Q; and
$R^{N4}$ is hydrogen or is absent or together with $R^{N1}$ forms a chemical bond.

Preferred skeletons of the formula I are those in which $R^{N2}$ and $R^{N3}$ together with the atoms to which they are bound form a 5- to 7-membered heterocyclic ring, in particular a 5- or 6-membered heteroaromatic ring, which may be fused with one, two or three further rings, in particular a cyclic group Q.

Accordingly, the polydentate nitrogen ligand preferably has a skeleton having the formula II,

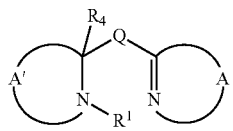

(II)

where A, Q, $R^{N1}$ and $R^{N4}$ are as defined above and A' together with the fragment —$NR^{N1}$—$CR^{N4}$— to which it is bound forms a 5- to 7-membered heterocyclic ring, in particular a 5- or 6-membered heteroaromatic ring, which may be fused with one, two or three further rings.

Preferred skeletons of the formulae I and II are those in which $R^{N1}$ together with $R^{N4}$ forms a chemical bond.

Preferred ligands are those which have a skeleton of the formula I or II in which the ring A or one of the rings A is 2-pyridyl or, when A is fused with Q, a b-pyridino group.

In the formulae I and II, Q is preferably a chemical bond or a 6-membered carbocycle which is ortho-fused with the group A.

Particularly preferred skeletons of the formula I are, in particular, 2,2'-bipyridine (A is 2-pyridyl and Q is a chemical bond) and 1,10-phenanthroline (A is b-pyrido and Q is a benzene ring which is ortho-fused with the pyrido groups).

Examples of preferred skeletons of the formulae I and II are the structures III.1 to III.9 shown by way of example below:

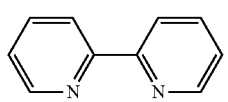

III.1

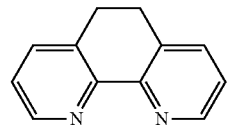

III.2

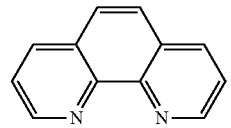

III.3

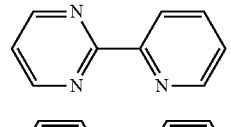

III.4

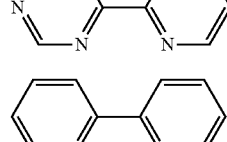

III.5

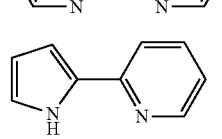

III.6

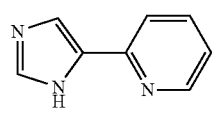

III.7

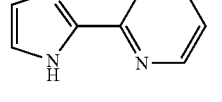

III.8

III.9

Among these, preference is given to ligands which have a skeleton of the formulae III.1 or III.2 and in particular a skeleton of the formula III.3.

The skeletons of the formulae I, II and III.1 to III.9 can have one or more substituents $R^s$, e.g. 1, 2, 3 or 4 substituents $R^s$, which are, for example, selected from among hydroxy, mercapto, $NE^1E^2$, $C(O)NE^1E^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl, cycloalkyl, heterocycloalkyl, aryl, hetaryl, cycloalkoxy, heterocycloalkoxy, aryloxy, hetaryloxy, arylthio, hetarylthio, cycloalkoxycarbonyl, heterocycloalkoxycarbonyl, aryloxycarbonyl and hetaryloxycarbonyl, where the cyclic groups in the latter fourteen radicals are unsubstituted or can have one or more radicals selected from among hydroxy, mercapto, $NE^1E^2$, $C(O)NE^1E^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl, cycloalkyl, heterocycloalkyl, aryl, hetaryl, cycloalkoxy, heterocycloalkoxy, aryloxy, hetaryloxy, cycloalkoxycarbonyl, heterocycloalkoxycarbonyl, aryloxycarbonyl, hetaryloxycarbonyl, where $E^1$ and $E^2$ are as defined above.

Preferred substituents $R^s$ on the skeletons of the formulae I, II and III.1 to III.9 are halogen, CN, $NO_2$, alkyl, alkoxy, alkylthio, acyl, cycloalkyl, cycloalkoxy, aryl, aryloxy and arylthio, in particular those selected from among $C_1$-$C_8$-alkyl, $C_1$-$C_8$-alkoxy, $C_1$-$C_8$-alkylthio, cyclohexyl, cyclohexyloxy, phenyl, phenoxy and phenylthio, where aryl, aryloxy, arylthio and phenyl, phenoxy and phenylthio are unsubstituted or may bear 1 or 2 of the abovementioned substituents selected, in particular, from among halogen, alkyl, haloalkyl, alkoxy and haloalkoxy.

Very particular preference is given to using 1,10-phenanthroline derivatives of the formula IV,

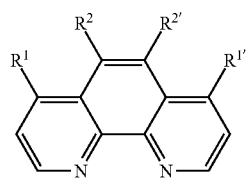

(IV)

where $R^1$ and $R^{1'}$ are each, independently of one another, hydrogen, hydroxy, mercapto, $NE^1E^2$, $C(O)NE^1E^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl, cycloalkyl, heterocycloalkyl, aryl, hetaryl, cycloalkoxy, heterocycloalkoxy, aryloxy, hetaryloxy, arylthio, hetarylthio, cycloalkoxycarbonyl, heterocycloalkoxycarbonyl, aryloxycarbonyl or hetaryloxycarbonyl, where the cyclic groups in the latter fourteen radicals are unsubstituted or have one or more radicals selected from among hydroxy, mercapto, $NE^1E^2$, $C(O)NE^1E^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl, cycloalkyl, heterocycloalkyl, aryl, hetaryl, cycloalkoxy, heterocycloalkoxy, aryloxy, hetaryloxy, cycloalkoxycarbonyl, heterocycloalkoxycarbonyl, aryloxycarbonyl, hetaryloxycarbonyl, where $E^1$ and $E^2$ are identical or different radicals selected from among hydrogen, alkyl, cycloalkyl and aryl or $E^1$ and $E^2$ together with the nitrogen atom to which they are bound form a saturated nitrogen heterocyclyl group which is unsubstituted or has one or more alkyl groups as substituents, and as polydentate ligands.

Preference is given to at least one or in particular both of the radicals $R^1$ and $R^{1'}$ being different from hydrogen. Preference is given to both the radicals $R^1$ and $R^{1'}$ being selected from among hydroxy, mercapto, alkyl, alkoxy, alkylthio, cycloalkyl, cycloalkoxy, aryl, aryloxy and arylthio, in particular from among $C_1$-$C_8$-alkyl, $C_1$-$C_8$-alkoxy, $C_1$-$C_8$-alkylthio, cyclohexyl, cyclohexyloxy, phenyl, phenoxy and phenylthio, where aryl, aryloxy, arylthio and phenyl, phenoxy and phenylthio are unsubstituted or may bear 1 or 2 of the abovementioned radicals selected, in particular, from among halogen, alkyl, haloalkyl, alkoxy and haloalkoxy.

In particular, the two radicals $R^1$ and $R^{1'}$ are each aryl, in particular phenyl, where aryl and phenyl are unsubstituted or may bear 1 or 2 radicals selected from among halogen, alkyl, haloalkyl, alkoxy and haloalkoxy.

Preference is given to the radicals $R^2$ and $R^{2'}$ each being, independently of one another, hydrogen, alkyl, halogen, nitro, acyl or cyano. In particular, $R^2$ and $R^{2'}$ are each hydrogen.

Particular preference is given to ligands of the formula IV in which $R^1$ and $R^{1'}$ are each aryl, in particular phenyl, where aryl and phenyl are unsubstituted or may bear 1 or 2 radicals selected from among halogen, alkyl, haloalkyl, alkoxy and haloalkoxy, with particular preference being given to aryl and phenyl being unsubstituted and $R^2$ and $R^{2'}$ being hydrogen.

A very particularly preferred polydentate nitrogen ligand is 4,7-diphenyl-1,10-phenanthroline.

In preferred embodiments, the copper complex has at least one further ligand selected from among amines, phosphines, N-heterocyclic carbenes, nitriles, olefins and mixtures thereof. Among these, particular preference is given to phosphine ligands, in particular those which have 1 phosphorus atom.

Copper(I) complexes which comprise a nitrogen ligand of the formula IV and at least one phosphine ligand, in which the radicals $R^1$ and $R^{1'}$ in the nitrogen ligand of the formula IV are different from hydrogen (hereinafter referred to as ligands of the formula IV'), are novel and are likewise provided by the present invention, with the exception of (4,7-diphenyl-1,10-phenanthroline)bis(triphenylphosphine)copper(I) tetrafluoroborate.

Preferred copper complexes thus correspond to the formula V

where (N,N) represents a bidentate N,N-ligand, in particular a ligand of the formula I and especially a ligand of the formula IV, L is a phosphine ligand, n is an integer from 1 to 3 and $X^-$ is one equivalent of an anion, e.g. of one of the above anions.

The phosphine ligand is preferably selected from among compounds of the formula VI

where $R^a$, $R^b$ and $R^c$ are each, independently of one another, alkyl, cycloalkyl, heterocycloalkyl, aryl or hetaryl, where the alkyl radicals can have 1, 2, 3, 4 or 5 substituents selected from among cycloalkyl, heterocycloalkyl, aryl, hetaryl, alkoxy, cycloalkoxy, heterocycloalkoxy, aryloxy, hetaryloxy, COOH, carboxylate, $SO_3H$, sulfonate, $NE^1E^2$, halogen, nitro, acyl and cyano, where $E^1$ and $E^2$ are as defined above and the cycloalkyl, heterocycloalkyl, aryl and hetaryl radicals can have 1, 2, 3, 4 or 5 substituents selected from among alkyl and the substituents mentioned above for the alkyl radicals $R^a$, $R^b$ and $R^c$, where $R^a$ and $R^b$ together with the phosphorus atom to which they are bound can also form a 5- to 8-membered P-heterocycle which is optionally additionally fused with one, two or three cycloalkyl, heterocycloalkyl, aryl or hetaryl groups, where the heterocycle and, if present, the fused-on groups can each independently bear one, two, three or four substituents selected from among alkyl and the substituents mentioned above for the alkyl radicals $R^a$, $R^b$ and $R^c$.

In particular, the at least one further ligand is selected from among triarylphosphines. Tri(p-fluorophenyl)phosphine is particularly preferred.

The process of the invention can be carried out in bulk or in the presence of a solvent and in bulk, with the latter being preferred.

Suitable solvents are, for example, aliphatic hydrocarbons such as pentane, hexane, heptane, octane or cyclohexane;

aromatic hydrocarbons such as benzene, toluene, xylenes, ethylbenzene or mesitylene;

amides such as dimethylformamide, diethylformamide, N-methylpyrrolidone, Nethylpyrrolidone or dimethylacetamide;

ureas such as tetramethylurea, N,N-dimethylimidazolinone (DMI) and N,N-dimethylpropyleneurea (DMPU);
nitriles such as acetonitrile or propionitrile;
sulfoxides such as dimethyl sulfoxide;
sulfones such as sulfolane;
alcohols such as methanol, ethanol, propanol or isopropanol;
esters such as methyl acetate, ethyl acetate, t-butyl acetate;
carbonates such as diethyl carbonate, ethylene carbonate and propylene carbonate; and
ethers such as dioxane, tetrahydrofuran, diethyl ether, dibutyl ether, methyl t-butyl ether, diisopropyl ether or diethylene glycol dimethyl ether.

If desired, a combination of a plurality of solvents can also be used.

Preference is given to using aromatic hydrocarbons, amides, ureas, esters and ethers and mixtures thereof as solvents. Particular preference is given to using solvents and solvent mixtures comprising amides and/or ureas, where the proportion of the amides and/or ureas is preferably at least 50% by volume of the solvent used for the reaction. Very particular preference is given to using solvents and solvent mixtures comprising amides selected from the group consisting of dimethylformamide, diethylformamide, N-methylpyrrolidone, dimethylacetamide, where the proportion of these amides is preferably at least 50% by volume of the solvent used for the reaction.

In the process of the invention, the copper complexes can, if desired, be used in preformed form and be generated directly in the reaction mixture from suitable copper precursors and the corresponding ligands. Preference is given to using preformed copper complexes.

In the process of the invention, a substoichiometric amount of catalyst is generally used, with the amount of catalyst typically being not more than 50 mol %, frequently not more than 20 mol % and in particular not more than 10 mol % or not more than 5 mol %, based on the alkyne. An amount of catalyst of from 0.001 to 50 mol %, frequently from 0.001 mol % to 20 mol % and in particular from 0.005 to 5 mol %, based on the alkyne, is generally used in the process of the invention. Preference is given to using an amount of catalyst of from 0.01 to 2 mol % and particularly preferably from 0.01 mol % to 1 mol %. All amounts of catalyst indicated are calculated as Cu and based on the amount of alkyne.

The process of the invention is generally carried out at temperatures in the range from −20° C. to 200° C., preferably in the range from 20° C. to 80° C. and particularly preferably in the range from 35° C. to 50° C. Temperatures below 60° C. have surprisingly been found to be particularly advantageous. At higher temperatures, as used in other processes, these catalysts preferentially catalyze the backreaction (decarboxylation).

The carbon dioxide is preferably used in the gaseous state in the process of the invention. Particular preference is given to using $CO_2$ partial pressures of from 0.1 to 20 bar and very particularly preferably 1-10 bar.

Bases used in the process of the invention are preferably bases whose corresponding acid is significantly stronger than the terminal alkyne used, so that the terminal alkyne is not quantitatively deprotonated by the base. Preference is given to using bases whose corresponding acid has a $pK_a$ which is at least 3 pK units, in particular at least 5 pK units and especially at least 8 pK units, e.g. from 3 to 22 pK units, in particular from 5 to 22 pK units, especially from 8 to 20 pK units, below the $pK_a$ of the terminal alkyne used. Particular preference is given to bases whose corresponding acid has a $pK_a$ in the range from 4 to 20 and in particular in the range from 5 to 15. The $pK_a$ values indicated here are the negative logarithm to the base ten of the acid constant determined at 25° C. in water or extrapolated to water. Preferred bases are oxo bases, i.e. the basic center to which the abstracted proton binds is an oxygen atom. In particular, inorganic salts are used as bases. Preference is given to using inorganic bases selected from the group consisting of alkali metal and alkaline earth metal hydroxides, carbonates, bicarbonates, oxides, phosphates, hydrogenphosphates, fluorides and carboxylates, e.g. acetates. Particular preference is given to using bases selected from the group consisting of alkali metal phosphates and alkaline earth metal phosphates, alkali metal carbonates and alkaline earth metal carbonates and alkali metal carboxylates and alkaline earth metal carboxylates, e.g. alkali metal and alkaline earth metal acetates. Very particular preference is given to using alkali metal carbonates such as sodium carbonate, potassium carbonate or cesium carbonate. Particular preference is likewise given to using alkali metal phosphates such as potassium phosphate. The base is generally used in an at least stoichiometric amount, based on the terminal alkyne used, preferably in a superstoichiometric amount, e.g. in an amount of from 1.1 mol to 10 mol, especially from 1.1 to 3 mol, per mole of terminal alkyne.

To isolate the products prepared according to the invention, the reaction mixture is, after the reaction is complete, preferably worked up by distillation and/or by extraction or crystallization. The products are isolated, as a matter of choice, as carboxylate salts or as free acids.

As an alternative, the carboxylic acid salts initially obtained can be converted into the corresponding alkyl esters directly in the reaction mixture by addition of alkylating agents selected from the group consisting of alkyl halides, alkyl sulfonates and dialkyl sulfates.

The invention is illustrated by the following examples.
The following abbreviations are used:
DMF=N,N-dimethylformamide
DMAc=N,N-dimethylacetamide
DMPU=N,N'-dimethylpropyleneurea
DMI=N,N'-dimethylimidazolin-2-one
THF=tetrahydrofuran
NMP=N-methylpyrrolidone
p-Me-$C_6H_4$=4-tolyl
p-MeO-$C_6H_4$=4-methoxyphenyl
p-Cl—$C_6H_4$=4-chlorophenyl
p-F—$C_6H_4$=4-fluorophenyl
Cy=cyclohexyl
Ph=$C_6H_5$=phenyl
JohnPhos=2-(di-tert-butylphosphino)biphenyl
Phen=1,10-phenanthroline
DiPhPhen=4,7-diphenyl-1,10-phenanthroline

EXAMPLES

Example 1

Synthesis of 1-α-nonynoic acid (4,7-Diphenyl-1,10-phenanthroline)bis(triphenylphosphine)copper(I) nitrate (19.7 mg, 0.02 mmol) and cesium carbonate (782 mg, 2.00 mmol) were placed in a flask. The reaction vessel was flushed with nitrogen and closed by means of a septum. Degassed DMF (3.00 ml) was subsequently added and the resulting mixture was stirred for 5 minutes at room temperature. After repeated evacuation and refilling of the reaction vessel with $CO_2$, 1-octyne (149 μL, 1.00 mmol) was injected. The reaction mixture was stirred at 50° C. and 1 bar of $CO_2$ pressure for 12 hours. After the reaction time had elapsed, the reaction mixture was cooled to room temperature, diluted with water and extracted three times with 100 ml each time of n-hexane. The aqueous fraction was admixed with dilute HCl (1N, 10.0 ml) and subsequently extracted three times with 100 ml each time of ethyl acetate. The combined organic fractions were washed with LiCl solution (1N, 10.0 ml) and saturated NaCl solution, dried over magnesium sulfate and filtered. The solvent was removed on a rotary evaporator to give a colorless oil (146 mg, 95%) which had a boiling point of 123° C./3 mbar and was identified as the expected reaction product. 1H NMR (600 MHz, $CDCl_3$) δ=2.34 (t, J=7.2 Hz, 2H), 1.55-1.60 (m, 2H), 1.38 (d, J=7.6 Hz, 2H), 1.25-1.32 (m, 4H) 0.88 (t, J=7.0 Hz, 3H) ppm. $^{13}C$ NMR (151 MHz, $CDCl_3$) δ=158.3, 92.8, 72.6, 31.1, 28.5, 27.3, 22.4, 18.8, 14.0 ppm. Anal. calc. for $C_9H_{14}O_2$: C, 70.1; H, 9.15. found: C, 70.2; H, 9.3.

Example 2

Synthesis of Phenylpropiolic Acid (4,7-Diphenyl-1,10-phenanthroline)bis[tris(p-fluorophenyl)phosphine]copper(I) nitrate (10.9 mg, 0.01 mmol) and cesium carbonate (391 mg, 1.20 mmol) were placed in a flask. The reaction vessel was then flushed with nitrogen and closed by means of a septum. Degassed DMF (3.00 ml) was subsequently added and the resulting mixture was stirred for 5 minutes at room temperature. After repeated evacuation and admission of $CO_2$ into the reaction vessel, phenylacetylene (110 μL, 1.00 mmol) was injected. The reaction mixture was stirred at 35° C. and 5 bar of $CO_2$ pressure in a steel autoclave for 12 hours. After the reaction time had expired, the reaction mixture was cooled to room temperature, diluted with water and extracted three times with 100 ml each time of n-hexane. The aqueous fraction was admixed with dilute HCl (1N, 10.0 ml), forming a colorless solid which was filtered off and purified further by recrystallization from water and ethanol. The purified colorless solid (143 mg, 98%) having a melting point of 133-134° C. could be identified as the desired reaction product.

$^1H$ NMR (400 MHz, $CDCL_3$) δ=7.04 (d, J=7.4 Hz, 2H), 6.95 (t, J=7.2 Hz, 1H), 6.88 (t, J=7.2 Hz, 2H) ppm. $^{13}C$ NMR (101 MHz, methanol-d4) δ=156.7, 133.7, 131.6, 129.7 120.9, 86.4, 74.2 ppm. Anal. calc. for $C_9H_6O_2$: C, 73.9; H, 4.1. found: C, 73.7; H, 4.3.

Examples 3-22

In examples 3-22, 1 mmol of alkyne was in each case reacted with 1 mol % of Cu(I) source (formula 2) in the presence of 1 mol % of ligand and 2.0 mmol of $Cs_2CO_3$. 3 ml of DMF were used in each case. After the reaction time had elapsed, the products were esterified by means of methyl iodide and characterized by means of GC/GC-MS. The catalysts I to X used are summarized in Table 1, and the results are summarized in Table 2.

TABLE 1

Copper(I) complexes

| | |
|---|---|
| I: | R = $C_6H_5$; n = 2 |
| V: | R = p-MeO—$C_6H_4$; n = 2 |
| VI: | R = p-Me—$C_6H_4$; n = 2 |
| VII: | R = Cy; n = 2 |
| VIII: | R = JohnPhos; n = 1 |
| IX: | R = p-Cl—$C_6H_4$; n = 2 |
| X: | R = p-F—$C_6H_4$; n = 2 |

| | |
|---|---|
| II: | $R^1, R^{1'}, R^2$ = H |
| III: | $R^1, R^{1'}$ = Cl; $R^2$ = H |
| IV: | $R^1, R^{1'}$ = H; $R^2$ = $NO_2$ |

TABLE 2

$$R^x\text{—}\!\!\equiv\!\!\text{—} + CO_2 \xrightarrow[\text{Base, DMF}]{Cu(I)\ cat} R^x\text{—}\!\!\equiv\!\!\text{—}COOH$$

| # | 1 | Cu(I) cat | Base | $CO_2$ [bar] | T [° C.] | t [h] | Yield [%] |
|---|---|---|---|---|---|---|---|
| 3 | 1a | CuI/Phen | $Cs_2CO_3$ | 1 | 100 | 8 | 52 |
| 4 | 1a | CuI/diPhPhen | $Cs_2CO_3$ | 1 | 100 | 8 | 64 |
| 5* | 1a | CuI/$PPh_3$ | $Cs_2CO_3$ | 1 | 100 | 8 | 40 |
| 6 | 1a | I | $Cs_2CO_3$ | 1 | 100 | 8 | 74 |
| 7 | 1a | I | $Cs_2CO_3$ | 1 | 80 | 8 | 80 |
| 8 | 1a | I | $Cs_2CO_3$ | 1 | 50 | 8 | 92 |
| $9^{a),b)}$ | 1a | I | $Cs_2CO_3$ | 1 | 50 | 8 | 93 |
| $10^{b)}$ | 1b | I | $Cs_2CO_3$ | 1 | 50 | 8 | 65 |
| $11^{b)}$ | 1b | I | $Cs_2CO_3$ | 5 | 35 | 8 | 85 |
| $12^{b)}$ | 1b | I | $Cs_2CO_3$ | 5 | 35 | 2 | 52 |
| $13^{b)}$ | 1b | II | $Cs_2CO_3$ | 5 | 35 | 2 | 53 |
| $14^{b)}$ | 1b | III | $Cs_2CO_3$ | 5 | 35 | 2 | 43 |
| $15^{b)}$ | 1b | IV | $Cs_2CO_3$ | 5 | 35 | 2 | 43 |
| $16^{b)}$ | 1b | V | $Cs_2CO_3$ | 5 | 35 | 2 | 49 |
| $17^{b)}$ | 1b | VI | $Cs_2CO_3$ | 5 | 35 | 2 | 52 |
| $18^{b)}$ | 1b | VII | $Cs_2CO_3$ | 5 | 35 | 2 | 46 |
| $19^{b)}$ | 1b | VIII | $Cs_2CO_3$ | 5 | 35 | 2 | 22 |
| $20^{b)}$ | 1b | IX | $Cs_2CO_3$ | 5 | 35 | 2 | 58 |
| $21^{b)}$ | 1b | X | $Cs_2CO_3$ | 5 | 35 | 2 | 85 |
| $22^{b)}$ | 1b | X | $Cs_2CO_3$ | 5 | 35 | 8 | 99 |

1a: $R^x$ = $CH_3(CH_2)_5$
1b: $R^x$ = Phenyl
$^{a)}$2 mol % of Cu(I) catalyst.
$^{b)}$1.2 mmol of base.
*not accroding to the invention In examples 3 and 4, the catalysts were generated in situ from copper(I) iodide and nitrogen ligands. In these cases, too, product is obtained but the yields remain below that in example 1 in which a preformed complex having nitrogen and phosphine ligands was used for the same reaction.

In example 5, exclusively phosphine ligands were added and in this case, too, the yields are significantly lower than in example 1.

In examples 6-9, temperatures, amounts of substrate per amount of catalyst and amount of base were varied, and it is found that a stoichiometric amount of base is sufficient and that the reaction gives particularly good yields in the range from 50° C. to 80° C.

In examples 10-12, it was shown that the best yields are achieved for alkynes having an aryl substituent at an elevated $CO_2$ pressure of about 5 bar and at low temperatures of about 35° C.

In examples 12-15, it was demonstrated that phenanthrolines are advantageous ligands and that substituents on the phenanthroline can have a positive influence on the yields. The best yields are obtained using 4,7-diphenyl-1,10-phenanthroline.

In examples 4, 12, 16-21, it was shown that phosphines as additional ligands have a positive influence on the yields. Triarylphosphines are advantageous, and the best yields were obtained using tri(p-fluorophenyl)phosphine.

In example 22, it was demonstrated that, at a reaction time of 8 hours, the equilibrium is shifted virtually quantitatively to the side of the products when a (4,7-diphenyl-1,10-phenanthroline)bis[tris(p-fluorophenyl)phosphine]copper(I) complex is used.

Examples 23-27

In examples 23-27 (Table 3) 1.00 mmol of alkyne was in each case reacted with 1 mol % of CuI in the presence of 1 mol % of 4,7-diphenyl-1,10-phenanthroline and 6.00 mmol of $K_2CO_3$ at 60° C. at 10 bar of $CO_2$ pressure for 2 hours. 3.00 ml of solvent were used in each case. After the reaction time had elapsed, the products were esterified by means of methyl iodide and characterized by means of GC/GC-MS.

TABLE 3

Influence of solvent.

| # | Solvent | Yield [%] |
|---|---------|-----------|
| 23 | DMF | 88 |
| 24 | DMAc | 49 |
| 25 | DMPU | 16 |
| 26 | NMP | 49 |
| 27 | DMI | 30 |

Comparative Example 28

Attempted Preparation of 1-α-Nonynoic Acid Using the Copper Catalysts Described by Inuoe Potassium carbonate (830 mg, 6 mmol) and copper(I) iodide (7.6 mg, 0.04 mmol) were placed in a flask. The reaction vessel was then flushed with nitrogen and closed by means of a septum. Degassed DMAc (3.00 ml) was subsequently added and the resulting mixture was stirred for 5 minutes at room temperature. After repeated evacuation and admission of $CO_2$ into the reaction vessel, 1-octyne (149 µL, 1.00 mmol) was injected. The reaction mixture was stirred at 100° C. and 1 bar of $CO_2$ pressure for 4 hours. After the reaction time had elapsed, the reaction mixture was cooled, and mixed with methyl iodide and analyzed by means of gas chromatography. Despite this interruption before work-up of the reaction mixture, only 34% of 1-α-nonynoic acid in the form of the corresponding methyl ester were detected in addition to 1-octyne. This confirms that a preparation of propiolic acids by the process of Inuoe would be relatively inefficient because of the unfavorable position of the equilibrium and the resulting unsatisfactory yields.

When 1.2 mmol of base and 0.01 mmol of copper(I) iodide were used, only 18% of 1-α-nonynoic acid in the form of the corresponding methyl ester were detected in addition to 1-octyne under otherwise identical conditions. Comparison with example 1, in which the product was obtained in a yield of 95% using the same amount of base and catalyst, clearly indicates the advance which has been achieved by the novel catalyst system and the novel reaction conditions.

Examples 29-32

General Experimental Description for the Synthesis of Aliphatic Propiolic Acids (4,7-Diphenylphenanthroline)bis(triphenylphosphine) copper(I) nitrate (19.7 mg, 0.02 mmol) and cesium carbonate (782 mg, 2.00 mmol) are placed in a flask. The reaction vessel is then flushed with nitrogen and closed by means of a septum. Degassed DMF (3.00 ml) is subsequently added and the resulting mixture is stirred at room temperature for 5 minutes. After repeated evacuation and refilling of the reaction vessel with $CO_2$, the aliphatic alkyne (1.00 mmol) is injected. The reaction mixture is subsequently stirred at 50° C. and 1 bar of $CO_2$ pressure for 12 hours. After the reaction time has elapsed, the reaction mixture is cooled to room temperature.

Work-Up:

The reaction mixture is diluted with water and extracted three times with 100 ml each time of n-hexane. The aqueous fraction is admixed with dilute HCl (1N, 10.0 ml) and subsequently extracted three times with 100 ml each time of ethyl acetate. The combined organic fractions are washed with LiCl solution (1N, 10.0 ml) and saturated NaCl solution, dried over magnesium sulfate and filtered. The solvent is removed on a rotary evaporator, leaving the product as solid or oil.

Example 29

4-Cyclohexylbut-2-ynoic acid

4-Cyclohexylbut-2-ynoic acid was prepared from 3-cyclohexyl-1-propyne (122 mg, 1.00 mmol) according to the general experimental description. After recrystallization from water and ethanol, 4-cyclohexylbut-2-ynoic acid is obtained as a colorless sold (141 mg, 85%) having a melting point of 85° C. $^1$H NMR (400 MHz, CDCl$_3$): δ=10.46 (s, 1H), 2.24 (d, J=6.7 Hz, 2H), 1.79 (d, J=12.9 Hz, 2H), 1.71 (d, J=12.9 Hz, 2H), 1.64 (d, J=12.1 Hz, 1H), 1.56 (ddd, J=10.7, 7.1, 4.1 Hz, 1H), 1.17-1.26 (m, 2H), 0.95-1.06 (m, 2H) ppm. $^{13}$C NMR (101 MHz, CDCl$_3$): δ=158.4, 91.8, 80.6, 77.4, 77.1, 76.8, 36.6, 32.7, 26.5, 26.0, 26.0, 21.1, 14.2 ppm. Anal. calc. for $C_{10}H_{14}O_2$: C, 72.2; H, 8.5. Found: C, 71.9; H, 8.1.

Example 30

4-Methoxy-2-butynoic acid

4-Methoxy-2-butynoic acid was prepared from 3-methoxy-1-propyne (84 µL, 1.00 mmol) according to the general experimental description. This gives 4-methoxy-2-butynoic acid (66 mg, 58%) as a colorless oil. The analytical data (NMR, IR) agreed with the literature values for 4-methoxy-2-butynoic acid [CAS: 24303-68-8].

Example 31

4-Methylpent-4-en-2-ynoic acid

4-Methylpent-4-en-2-ynoic acid was prepared from 2-methyl-1-buten-3-yne (98 μL, 1.00 mmol) according to the general experimental description. This gives 4-methylpent-4-en-2-ynoic acid (106 mg, 97%) as a colorless oil. The analytical data (NMR, IR) agreed with the literature values for 4-methylpent-4-en-2-ynoic acid [CAS: 5963-81-5].

Example 32

5-Phenylpent-2-ynoic acid

5-Phenylpent-2-ynoic acid was prepared from 4-phenyl-1-butyne (141 μL, 1.00 mmol) according to the general experimental description. This gives 5-phenylpent-2-ynoic acid (170 mg, 97%) as a colorless oil. The analytical data (NMR, IR) agreed with the literature values for 5-phenylpent-2-ynoic acid [CAS: 3350-93-4].

Examples 33-40

In the case of aromatic propiolic acids, better yields were obtained when somewhat higher $CO_2$ pressures were used. This increasing pressure has no advantages in the preparation of aliphatic propiolic acids.

General Experimental Description for the Synthesis of Aromatic Propiolic Acids:

(4,7-Diphenylphenanthroline)bis[tris(p-fluorophenyl)phosphine]copper(I) nitrate (10.9 mg, 0.01 mmol) and cesium carbonate (391 mg, 1.20 mmol) are placed in a flask. The reaction vessel is then flushed with nitrogen and closed by means of a septum. Degassed DMF (3.00 ml) is subsequently added and the resulting mixture is stirred at room temperature for 5 minutes. After repeated evacuation and refilling of the reaction vessel with $CO_2$, the aromatic alkyne (1.00 mmol) is injected. The reaction mixture is subsequently stirred at 35° C. and 5 bar of $CO_2$ pressure in a steel autoclave for 12 hours. After the reaction time has elapsed, the reaction mixture is cooled to room temperature.

Work-Up:

The reaction solution is diluted with water and extracted three times with 100 ml each time of n-hexane. The aqueous fraction is admixed with dilute HCl (1N, 10.0 ml), forming a solid which is filtered off and purified further by recrystallization from water and ethanol.

Example 33

(4-Methylphenyl)propiolic acid (4-Methylphenyl)propiolic acid was prepared from (4-methylphenyl)acetylene (127 μL, 1.00 mmol) according to the general experimental description. This gives (4-methylphenyl)propiolic acid (160 mg, 99%) as a colorless solid. The analytical data (NMR, IR) agreed with the literature values for (4-methylphenyl)propiolic acid [CAS: 2227-58-9].

Example 34

(4-Methoxyphenyl)propiolic acid (4-Methoxyphenyl)propiolic acid was prepared from (4-methoxyphenyl)acetylene (134 μL, 1.00 mmol) according to the general experimental description. This gives (4-methoxyphenyl)propiolic acid (143 mg, 81%) as a colorless solid. The analytical data (NMR, IR) agreed with the literature values for (4-methoxyphenyl)propiolic acid [CAS: 2227-57-8].

Example 35

(4-Trifluoromethylphenyl)propiolic acid (4-Trifluoromethylphenyl)propiolic acid was prepared from 4-ethynyl-α,α,α-trifluorotoluene (168 μL, 1.00 mmol) according to the general experimental description. This gives (4-trifluoromethylphenyl)propiolic acid (214 mg, 99%) as a colorless solid. The analytical data (NMR, IR) agreed with the literature values for (4-trifluoromethylphenyl)propiolic acid [CAS: 3792-88-9].

Example 36

(3-Bromo-4-methoxyphenyl)propiolic acid (3-Bromo-4-methoxyphenyl)propiolic acid was prepared from 2-bromo-4-ethynylanisole (218 μL, 1.00 mmol) according to the general experimental description. This gives (3-bromo-4-methoxyphenyl)propiolic acid (159 mg, 62%) as a colorless solid having a melting point of 50° C. $^1$H NMR (600 MHz, $d_6$-ethanol): δ=6.60 (s, 1H), 6.45 (s, 1H), 5.98 (s, 1H), 2.81 (s, 3H) ppm. $^{13}$C NMR (151 MHz, $d_6$-ethanol): δ=158.1, 137.1, 136.1, 133.9, 132.4, 112.0, 111.7, 111.3, 81.4, 77.4 ppm. Anal. calc. for $C_{10}H_7BrO_3$: C, 47.1; H, 2.7. Found: C, 4.4; H, 2.9.

Example 37

(3-Chlorophenyl)propiolic acid (3-Chlorophenyl)propiolic acid was prepared from 3-chloro-1-ethynylbenzene (127 μL, 1.00 mmol) according to the general experimental description. This gives (3-chlorophenyl)propiolic acid (155 mg, 86%) as a colorless solid. The analytical data (NMR, IR) agreed with the literature values for (3-chlorophenyl)propiolic acid [CAS: 7396-28-3].

Example 38

(2-Methylphenyl)propiolic acid (2-Methylphenyl)propiolic acid was prepared from (2-methylphenyl)acetylene (127 μL, 1.00 mmol) according to the general experimental description. This gives (2-methylphenyl)propiolic acid (139 mg, 87%) as a colorless solid. The analytical data (NMR, IR) agreed with the literature values for (2-methylphenyl)propiolic acid [CAS: 7515-27-7].

Example 39

(2-Methoxyphenyl)propiolic acid (2-Methoxyphenyl)propiolic acid was prepared from (2-methoxyphenyl)acetylene (129 μL, 1.00 mmol) according to the general experimental description. This gives (2-methoxyphenyl)propiolic acid (130 mg, 74%) as a colorless solid. The analytical data (NMR, IR) agreed with the literature values for (2-methoxyphenyl)propiolic acid [CAS: 7342-00-9].

Example 40

(4-Propylphenyl)propiolic acid (4-Propylphenyl)propiolic acid was prepared from (4-propylphenyl)acetylene (158 μL, 1.00 mmol) according to the general experimental description. This gives (4-propylphenyl)propiolic acid (140 mg, 74%) as a colorless solid having a melting point of 155-156° C. $^1$H NMR (400 MHz, d$_4$-methanol): δ=7.38 (d, J=7.8 Hz, 2H), 7.14, (d, J=7.8 Hz, 2H), 2.52 (t, J=7.6 Hz, 2H), 1.49-1.59 (m, 2H), 0.83 (t, J=7.2 Hz, 3H) ppm. $^{13}$C NMR (101 MHz, d$_4$-methanol): δ=156.6, 147.2, 133.7, 129.8, 117.9, 86.8, 81.3, 38.8, 25.2, 13.8 ppm. Anal. calc. for $C_{12}H_{12}O_2$: C, 76.5; H, 6.4. Found: C, 76.3; H, 6.7.

Example 41

Carboxylation of Acetylene (4,7-Diphenylphenanthroline)bis[triphenylphosphine]copper(I) nitrate (21.3 mg, 0.02 mmol), 1-bromohexane (282 μL, 2.00 mmol) and cesium carbonate (782 mg, 2.40 mmol) were placed in a flask. The reaction vessel was then flushed with nitrogen and closed by means of a septum. The degassed DMF (3.00 ml) was subsequently added, the resulting mixture is stirred at room temperature for 5 minutes and repeatedly supplied with $CO_2$ and evacuated. The reaction vessel was placed in a steel autoclave and an acetylene pressure of 1 bar was set. The reaction mixture was subsequently stirred at 60° C. and 5 bar of $CO_2$ pressure for 2 hours. After the reaction time had elapsed, the reaction mixture was cooled to room temperature, 50 μL of n-tetradecane were added, a 0.25 ml sample was taken, washed with 3 ml of ethyl acetate and 2 ml of water, 0.25 ml was taken, filtered through a pipette comprising $MgSO_4$ and analyzed. 7.5 mg of acetylenecarboxylic acid and 10.4 mg of acetylenedicarboxylic acid in the form of the n-hexyl ester were able to be detected in the reaction mixture.

Example 42

Carboxylation of Acetylene with Subsequent Addition of 1-Bromohexane (4,7-Diphenylphenanthroline)bis[triphenylphosphine]copper(I) nitrate (21.3 mg, 0.02 mmol) and cesium carbonate (782 mg, 2.40 mmol) were placed in a flask. The reaction vessel was then flushed with nitrogen and closed by means of a septum. Degassed DMF (3.00 ml) was subsequently added, the resulting mixture is stirred at room temperature for 5 minutes and repeatedly supplied with $CO_2$ and evacuated. The reaction vessel was placed in a steel autoclave and an acetylene pressure of 1 bar was set. The reaction mixture was subsequently stirred at 60° C. and 5 bar of $CO_2$ pressure for 2 hours. After the reaction time had elapsed, 1-bromohexane (282 μL, 2.00 mmol) was added to the reaction mixture and the mixture was heated at 60° C. for a further one hour. The mixture was subsequently cooled to room temperature, 50 μL of n-tetradecane were added, a 0.25 ml sample was taken, washed with 3 ml of ethyl acetate and 2 ml of water, 0.25 ml were taken, filtered through a pipette comprising $MgSO_4$ and analyzed. 7.3 mg of acetylenecarboxylic acid and 10.5 mg of acetylenedicarboxylic acid in the form of the n-hexyl ester were able to be detected in the reaction mixture.

Examples 43-49

General Method for the Preparation of Copper-Phosphine Complexes 2.00 ml of ethanol are placed in a Schlenk vessel and heated to reflux. The phosphine (3.00 mmol) is subsequently slowly added under an $N_2$ atmosphere until it has completely dissolved. Copper(II) nitrate trihydrate (242 mg, 1.00 mmol) is then added a little at a time to this mixture over a period of 20 minutes. After the addition is complete, the reaction mixture is heated to boiling for 30 minutes, resulting in a precipitate being formed. The precipitate is subsequently filtered off and washed with ethanol (2×10.0 ml) and cold (0° C.) diethyl ether. It is subsequently dried under reduced pressure ($2 \times 10^{-3}$ mm of Hg).

Example 43

Bis(triphenylphosphine)copper(I) nitrate

Bis(triphenylphosphine)copper(I) nitrate was prepared from triphenylphosphine (787 mg, 3.00 mmol) according to the general experimental description. This gave bis(triphenylphosphine)copper(I) nitrate (480 mg, 74%) as a light-green solid. $^{31}$P NMR (162 MHz, d$_6$-DMSO): δ=−3.56 (s, 2P) ppm. Anal. calc. for $C_{36}H_{30}CuNO_3P_2$: C, 66.5; H, 4.6; N, 2.1. Found: C, 66.1; H, 4.5; N, 2.1.

Example 44

Bis(tris(p-methoxyphenyl)phosphine)copper(I) nitrate

Bis(tris(p-methoxyphenyl)phosphine)copper(I) nitrate was prepared from tris(pmethoxyphenyl)phosphine (1.05 g, 3.00 mmol) according to the general experimental description. This gave bis(tris(p-methoxyphenyl)phosphine)copper(I) nitrate (712 mg, 86%) as a light-green solid. $^{31}$P NMR (162 MHz, CDCl$_3$): δ=28.69 (s, 1P), 19.36 (s, 1P) ppm. Anal. calc. for $C_{66}H_{58}CuN_3O_9P_2$: C, 68.2; H, 5.0; N, 3.6. Found: C, 67.4; H, 5.3; N, 3.5.

Example 45

Bis(tri-p-tolylphosphine)copper(I) nitrate

Bis(tri-p-tolylphosphine)copper(I) nitrate was prepared from tri-p-tolylphosphine (913 mg, 3.00 mmol). This gives bis(tri-p-tolylphosphine)copper(I) nitrate (390 mg, 54%) as a light-green solid. $^{31}$P NMR (162 MHz, CDCl$_3$): δ 27.06 (s, 1P)-36.45 (s, 1P) ppm. Anal. calc. for $C_{42}H_{42}CuNO_3P_2$: C, 68.7; H, 5.7; N, 1.9. Found: C, 68.4; H, 5.3; N, 1.9.

Example 46

Bis(tricyclohexylphosphine)copper(I) nitrate

Bis(tricyclohexylphosphine)copper(I) nitrate was prepared from tricyclohexylphosphine (841 mg, 3.00 mmol). This gives bis(tricyclohexylphosphine)copper(I) nitrate (389 mg, 57%) as a yellow solid. $^{31}$P NMR (162 MHz, CDCl$_3$): δ

13.22 (s, 2P) ppm. Anal. calc. for $C_{36}H_{66}CuNO_3P_2$: C, 63.0; H, 9.7; N, 2.0. Found: C, 62.8; H, 9.5; N, 2.1.

Example 47

[(O-biphenyl)di-tert-butylphosphine]copper(I) nitrate

[(O-Biphenyl)di-tert-butylphosphine]copper(I) nitrate was prepared from (O-biphenyl)di-tert-butylphosphine (1.34 g, 3.00 mmol). This gives [(O-biphenyl)di-tert-butylphosphine]copper(I) nitrate (630 mg, 99%) as a colorless solid. $^{31}$P NMR (162 MHz, CDCl$_3$): δ=51.54 (s, 2P) ppm. Anal. calc. for $C_{40}H_{54}CuNO_3P$: C, 56.7; H, 6.4; N, 3.3. Found: C, 57.0; H, 6.3; N, 3.4.

Example 48

Bis[tris(p-chlorophenyl)phosphine]copper(I) nitrate

Bis[tris(p-chlorophenyl)phosphine]copper(I) nitrate was prepared from tris(pchlorophenyl)phosphine (1.10 g, 3.00 mmol). This gives bis[tris(pchlorophenyl)phosphine]copper(I) nitrate (247 mg, 39%) as a colorless solid. Anal. calc. for $C_{36}H_{24}Cl_{6}CuNO_3P_2$: C, 50.47; H, 2.8; N, 1.6. Found: C, 50.19; H, 3.0; N, 2.0.

Example 49

Bis[tris(p-fluorophenyl)phosphine]copper(I) nitrate

Bis[tris(p-fluorophenyl)phosphine]copper(I) nitrate was prepared from tris(pfluorophenyl)phosphine (949 mg, 3.00 mmol). This gives bis[tris(pfluorophenyl)phosphine]copper(I) nitrate (560 mg, 74%) as a colorless solid. $^{31}$P NMR (162 MHz, CDCl$_3$): δ=19.86 (s, 2P) ppm. Anal. calc. for $C_{36}H_{24}CuF_6NO_3P_2$: C, 57.0; H, 3.2; N, 1.8. Found: C, 57.3; H, 3.2; N, 2.2.

Examples 50-58

General Experimental Description for the Synthesis of Mixed Ligand Copper Complexes The copper-phosphine complex (1.00 mmol) together with 10.0 ml of CHCl$_3$ is placed in a Schlenk vessel. The phosphine (1.00 mmol) is added to this solution until it is completely dissolved. A solution of the N-ligand (1.00 mmol) in 2 ml of CHCl$_3$ is then added over a period of 30 minutes. The mixture is subsequently stirred at room temperature for a further 30 minutes. After removal of the CHCl$_3$ in vacuo, the resulting solid is recrystallized from CH$_2$Cl$_2$ and Et$_2$O.

Example 50

(4,7-diphenyl-1,10-phenanthroline)bis(triphenylphosphine)copper(I) nitrate (4,7-Diphenyl-1,10-phenanthroline)bis(triphenylphosphine)copper(I) nitrate was prepared from bis(triphenylphosphine)copper(I) nitrate (650 mg, 1.00 mmol), 4,7-diphenyl-1,10-phenanthroline (339 mg, 1.00 mmol) and triphenylphosphine (262 mg, 1.00 mmol). This gives (4,7-diphenyl-1,10-phenanthroline)bis(triphenylphosphine)copper(I) nitrate (980 mg, 99%) as a yellow solid. $^{31}$P NMR (162 MHz, CDCl$_3$) δ=3.32 (s, 1P) ppm. Anal. calc. for $C_{48}H_{36}Cl_2CuN_3O_3P_2$: C, 59.8, H, 3.9, N, 4.3. Found: C, 59.0, H, 3.8, N, 4.6.

Example 51

(4,7-dichloro-1,10-phenanthroline)bis(triphenylphosphine)copper(I) nitrate (4,7-Dichloro-1,10-phenanthroline)bis(triphenylphosphine)copper(I) nitrate was prepared from bis(triphenylphosphine)copper(I) nitrate (650 mg, 1.00 mmol), 4,7-dichloro-1,10-phenanthroline (249 mg, 1.00 mmol) and triphenylphosphine (262 mg, 1.00 mmol). This gives (4,7-dichloro-1,10-phenanthroline)bis(triphenylphosphine)copper(I) nitrate (980 mg, 99%) as a light-brown solid. $^{31}$P NMR (162 MHz, CDCl$_3$): δ=2.62 (s, 2P) ppm. Anal. calc. for $C_{48}H_{36}C_{12}CuN_3O_3P_2$: C, 59.8; H, 3.89; N, 4.3. Found: C, 58.9; H, 3.8; N, 4.6.

Example 52

(5-Nitro-1,10-phenanthroline)bis(triphenylphosphine)copper(I) nitrate (5-Nitro-1,10-phenanthroline)bis(triphenylphosphine)copper(I) nitrate was prepared from bis(triphenylphosphine)copper(I) nitrate (650 mg, 1.00 mmol), 5-nitro-1,10-phenanthroline (232 mg, 1.00 mmol) and triphenylphosphine (262 mg, 1.00 mmol). This gives (5-nitro-1,10-phenanthroline)bis(triphenylphosphine)copper(I) nitrate (723 mg, 83%) as an orange solid. $^{31}$P NMR (162 MHz, DMSO-d$_6$): δ=–3.56 (s, 2P) ppm. Anal. calc. for $C_{48}H_{37}CuN_4O_5P_2$: C, 65.8; H, 4.2; N, 6.4. Found: C, 64.6; H, 4.2; N, 6.3.

Example 53

(4,7-diphenyl-1,10-phenanthroline)bis[tris(pmethoxyphenyl)phosphine]copper(I) nitrate (4,7-Diphenyl-1,10-phenanthroline)bis[tris(p-methoxyphenyl)phosphine]copper(I) nitrate was prepared from bis(tris(p-methoxyphenyl)phosphine)copper(I) nitrate (830 mg, 1.00 mmol), 4,7-diphenyl-1,10-phenanthroline (339 mg, 1.00 mmol) and tris(pmethoxyphenyl)phosphine (352 mg, 1.00 mmol). This gives (4,7-diphenyl-1,10-phenanthroline) bis[tris(p-methoxyphenyl)phosphine]copper(I) nitrate as a light-brown solid (1.03 g, 89%). $^{31}$P NMR (162 MHz, CDCl$_3$): δ=28.69 (s, 1P), 19.36 (s, 1P) ppm. Anal. calc. for $C_{66}H_{58}CuN_3O_9P_2$: C, 68.1; H, 5.0; N, 3.4. Found: C, 67.4; H, 5.3; N, 3.4.

Example 54

(4,7-diphenyl-1,10-phenanthroline)bis(tri-p-tolylphosphine)copper(I) nitrate (4,7-Diphenyl-1,10-phenanthroline)bis(tri-p-tolylphosphine)copper(I) nitrate was prepared from bis(tri-p-tolylphosphine)copper(I) nitrate (734 mg, 1.00 mmol), 4,7-diphenyl-1,10-phenanthroline (339 mg, 1.00 mmol) and tri-p-tolylphosphine (304 mg, 1.00 mmol). This gives (4,7-diphenyl-1,10-phenanthroline)bis(tri-p-tolylphosphine)copper(I) nitrate (891 mg, 76%) as a light-brown solid. $^{31}$P NMR (162 MHz, CDCl$_3$): δ=20.61 (s, 2P) ppm. Anal. calc. for $C_{66}H_{58}CuN_3O_3P_2$: C, 69.9; H, 5.25; N, 3.6. Found: C, 71.1; H, 5.4; N, 3.9.

Example 55

(4,7-diphenyl-1,10-phenanthroline)bis(tricyclohexylphosphine)copper(I) nitrate (4,7-Diphenyl-1,10-phenanthroline)bis(tricyclohexylphosphine)copper(I) nitrate was prepared from bis(tricyclohexylphosphine)copper(I) nitrate (686 mg, 1.00 mmol), 4,7-diphenyl-1,10-phenanthroline (339 mg, 1.00 mmol) and tricyclohexylphosphine (280 mg, 1.00 mmol). This gives (4,7-diphenyl-1,10-phenanthrolind)bis(tricyclohexylphosphine)copper(I) nitrate (867 mg, 85%) as a yellow solid. $^{31}$P NMR (162 MHz, CDCl$_3$): δ=50.11 (s, 1P), 33.76 (s, 1P) ppm. Anal. calc. for C$_{60}$H$_{82}$CuN$_3$O$_3$P$_2$: C, 70.7; H, 8.1; N, 4.1. Found: C, 69.8; H, 8.1; N, 3.9.

Example 56

[(4,7-diphenyl-1,10-phenanthroline)(o-biphenylyl) di-tert-butylphosphine]copper(I) nitrate

[(4,7-Diphenyl-1,10-phenanthroline)(o-biphenylyl)di-tert-butylphosphine]copper(I) nitrate was prepared from [(O-biphenylyl)di-tert-butylphosphine]copper(I) nitrate (423 mg, 1.00 mmol), 4,7-diphenyl-1,10-phenanthroline (339 mg, 1.00 mmol) and (O-biphenyl)di-tert-butylphosphine (298 mg, 1.00 mmol). This gives: [(4,7-diphenyl-1,10-phenanthroline)(o-biphenylyl)di-tert-butylphosphine]copper(I) nitrate (748 mg, 99%) as a yellow solid. $^{31}$P NMR (162 MHz, CDCl$_3$): δ=33.23 (s, 1P), 18.14 (s, 1P) ppm. Anal. calc. for C$_{64}$H$_{70}$CuN$_3$O$_3$P$_2$: C, 69.8; H, 5.7; N, 5.5. Found: C, 68.4; H, 5.8; N, 5.2.

Example 57

(4,7-diphenyl-1,10-phenanthroline)bis[tris(pchlorophenyl)phosphine)]copper(I) nitrate (4,7-Diphenyl-1,10-phenanthroline)bis[tris(p-chlorophenyl)phosphine)]copper(I) nitrate was prepared from bis[tris(p-chlorophenyl)phosphine]copper(I) nitrate (856 mg, 1.00 mmol), 4,7-diphenyl-1,10-phenanthroline (339 mg, 1.00 mmol) and tris(pchlorophenyl)phosphine (366 mg, 1.00 mmol). This gives (4,7-diphenyl-1,10-phenanthroline)bis[tris(p-chlorophenyl)phosphine)]copper(I) nitrate (852 mg, 72%) as a yellow solid. $^{31}$P NMR (162 MHz, CDCl$_3$): δ=−5.90 (s, 2P) ppm. Anal. calc. for C$_{60}$H$_{40}$Cl$_6$CuN$_3$O$_3$P$_2$: C, 60.6; H, 3.4; N, 3.5. Found: C, 60.3; H, 3.5; N, 3.9.

Example 58

(4,7-diphenyl-1,10-phenanthroline)bis[tris(pfluorophenyl)phosphine]copper(I) nitrate (4,7-Diphenyl-1,10-phenanthroline)bis[tris(p-fluorophenyl)phosphine]copper(I) nitrate was prepared from bis[tris(p-fluorophenyl)phosphine]copper(I) nitrate (758 mg, 1.00 mmol), 4,7-diphenyl-1,10-phenanthroline (339 mg, 1.00 mmol) and tris(pfluorophenyl)phosphine (316 mg, 1.00 mmol). This gives (4,7-diphenyl-1,10-phenanthroline)bis[tris(p-fluorophenyl)phosphine]copper(I) nitrate (1.4 g, 97%) as a yellow solid. $^{31}$P NMR (162 MHz, CDCl$_3$): δ=19.84 (s, 2P) ppm. Anal. calc. for C$_{60}$H$_{40}$CuF$_6$N$_3$O$_3$P$_2$: C, 66.1; H, 3.7; N, 3.8. Found: C, 65.4; H, 3.8; N, 4.0.

The invention claimed is:

1. A process for preparing a propiolic acid of formula (XI) or a metal salt or ester thereof,

$$R^x\text{—}C\equiv C\text{—}COOH \quad (XI)$$

wherein

R$^x$ is selected from the group consisting of a hydrogen, a COOR$^{x1}$, an alkyl optionally substituted by A substituent R$^{x3}$, an alkenyl optionally substituted by one or more substituents R$^{x3}$, a cycloalkyl optionally substituted by A substituent R$^{x4}$, a heterocycloalkyl optionally substituted by a substituent R$^{x4}$, an aryl optionally substituted by a substituent R$^{x4}$, a hetaryl optionally substituted by a substituent R$^{x4}$, and a (R$^{x2}$)$_3$Si, R$^{x1}$ is selected from the group consisting of hydrogen, alkyl, cycloalkyl, heterocycloalkyl, aryl, and hetaryl, wherein the alkyl, cycloalkyl, heterocycloalkyl, aryl, and hetaryl are unsubstituted or comprise at least one radical selected from the group consisting of hydroxy, mercapto, NE$^1$E$^2$, C(O)NE$^1$E$^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl and cycloalkyl, R$^{x2}$ is selected from the group consisting of alkyl, cycloalkyl, heterocycloalkyl, aryl, and hetaryl, wherein the cycloalkyl, heterocycloalkyl, aryl, and hetaryl are unsubstituted or comprise at least one radical selected from the group consisting of hydroxy, mercapto, NE$^1$E$^2$, C(O)NE$^1$E$^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl, and cycloalkyl, R$^{x3}$ is selected from the group consisting of halogen, cyano, hydroxy, mercapto, alkoxy, COOH, SO$_3$H, NE$^1$E$^2$, C(O)NE$^1$E$^2$, acyl, alkoxycarbonyl, cycloalkyl, heterocycloalkyl, aryl, hetaryl, cycloalkoxy, heterocycloalkoxy, aryloxy, hetaryloxy, cycloalkoxycarbonyl, heterocycloalkoxycarbonyl, aryloxycarbonyl, and hetaryloxycarbonyl, wherein the alkoxycarbonyl, cycloalkyl, heterocycloalkyl, aryl, hetaryl, cycloalkoxy, heterocycloalkoxy, aryloxy, hetaryloxy, cycloalkoxycarbonyl, heterocycloalkoxycarbonyl, aryloxycarbonyl, and hetaryloxycarbonyl are unsubstituted or comprise at least one radical selected from the group consisting of hydroxy, mercapto, NE$^1$E$^2$, C(O)NE$^1$E$^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl, and cycloalkyl, R$^{x4}$ is selected from the group consisting of halogen, cyano, nitro, hydroxy, mercapto, alkoxy, COOH, SO$_3$H, NE$^1$E$^2$, C(O)NE$^1$E$^2$, alkyl, haloalkyl, acyl, alkoxycarbonyl, cycloalkyl, heterocycloalkyl, aryl, hetaryl, cycloalkoxy, heterocycloalkoxy, aryloxy, hetaryloxy, cycloalkoxycarbonyl, heterocycloalkoxycarbonyl, aryloxycarbonyl and hetaryloxycarbonyl, wherein the alkoxycarbonyl, cycloalkyl, heterocycloalkyl, aryl, hetaryl, cycloalkoxy, heterocycloalkoxy, aryloxy, hetaryloxy, cycloalkoxycarbonyl, heterocycloalkoxycarbonyl, aryloxycarbonyl and hetaryloxycarbonyl are unsubstituted or comprise at least one radical selected from the group consisting of hydroxy, mercapto, NE$^1$E$^2$, C(O)NE$^1$E$^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl, and cycloalkyl, and $E^1$ and $E^2$ are each independently a radical selected from the group consisting of hydrogen, alkyl, cycloalkyl, and aryl, or $E^1$ and $E^2$ together with a nitrogen atom to which they are bound form a saturated nitrogen heterocyclyl which is unsubstituted or comprises an alkyl group as a substituent, the process comprising:

reacting a terminal alkyne with carbon dioxide in the presence of a base and a copper complex comprising a polydentate ligand that has a skeleton of one of the formulas (III.1), (III.2), and (III.3),

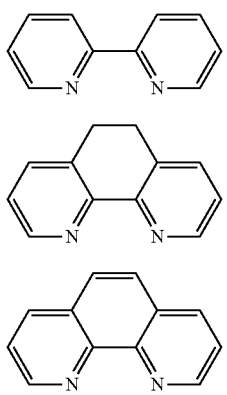

which can have a substituent $R^s$, which is selected from the group consisting of hydroxy, mercapto, $NE^1E^2$, $C(O)NE^1E^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl, cycloalkyl, heterocycloalkyl, aryl, hetaryl, cycloalkoxy, heterocycloalkoxy, aryloxy, hetaryloxy, arylthio, hetarylthio, cycloalkoxycarbonyl, heterocycloalkoxycarbonyl, aryloxycarbonyl and hetaryloxycarbonyl, where the cyclic groups in the latter fourteen radicals are unsubstituted or can have at least one radical selected from the group consisting of hydroxy, mercapto, $NE^1E^2$, $C(O)NE^1E^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl, cycloalkyl, heterocycloalkyl, aryl, hetaryl, cycloalkoxy, heterocycloalkoxy, aryloxy, hetaryloxy, cycloalkoxycarbonyl, heterocycloalkoxycarbonyl, aryloxycarbonyl, hetaryloxycarbonyl, and where $E^1$ and $E^2$ are as defined above, and a further ligand is a phosphine.

2. The process according to claim 1, wherein the terminal alkyne is a compound of formula:

wherein $R^x$ is selected from the group consisting of a hydrogen, a $COOR^{x1}$, an alkyl optionally substituted by a substituent $R^{x3}$, an alkenyl optionally substituted by a substituent $R^{x3}$, a cycloalkyl optionally substituted by a substituent $R^{x4}$, a heterocycloalkyl optionally substituted by a substituent $R^{x4}$, an aryl optionally substituted by a substituent $R^{x4}$, a hetaryl optionally substituted by a substituent $R^{x4}$, and a $(R^{x2})_3Si$, $R^{x1}$ is selected from the group consisting of hydrogen, alkyl, cycloalkyl, heterocycloalkyl, aryl, and hetaryl, wherein the alkyl, cycloalkyl, heterocycloalkyl, aryl, and hetaryl are unsubstituted or comprise at least one radical selected from the group consisting of hydroxy, mercapto, $NE^1E^2$, $C(O)NE^1E^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl and cycloalkyl, $R^{x2}$ is selected from the group consisting of alkyl, cycloalkyl, heterocycloalkyl, aryl, and hetaryl, wherein the cycloalkyl, heterocycloalkyl, aryl, and hetaryl are unsubstituted or comprise at least one radical selected from the group consisting of hydroxy, mercapto, $NE^1E^2$, $C(O)NE^1E^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl, and cycloalkyl, $R^{x3}$ is selected from the group consisting of halogen, cyano, hydroxy, mercapto, alkoxy, COOH, $SO_3H$, $NE^1E^2$, $C(O)NE^1E^2$, acyl, alkoxycarbonyl, cycloalkyl, heterocycloalkyl, aryl, hetaryl, cycloalkoxy, heterocycloalkoxy, aryloxy, hetaryloxy, cycloalkoxycarbonyl, heterocycloalkoxycarbonyl, aryloxycarbonyl, and hetaryloxycarbonyl, wherein the alkoxycarbonyl, cycloalkyl, heterocycloalkyl, aryl, hetaryl, cycloalkoxy, heterocycloalkoxy, aryloxy, hetaryloxy, cycloalkoxycarbonyl, heterocycloalkoxycarbonyl, aryloxycarbonyl, and hetaryloxycarbonyl are unsubstituted or comprise at least one radical selected from the group consisting of hydroxy, mercapto, $NE^1E^2$, $C(O)NE^1E^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl, and cycloalkyl, $R^{x4}$ is selected from the group consisting of halogen, cyano, nitro, hydroxy, mercapto, alkoxy, COOH, $SO_3H$, $NE^1E^2$, $C(O)NE^1E^2$, alkyl, haloalkyl, acyl, alkoxycarbonyl, cycloalkyl, heterocycloalkyl, aryl, hetaryl, cycloalkoxy, heterocycloalkoxy, aryloxy, hetaryloxy, cycloalkoxycarbonyl, heterocycloalkoxycarbonyl, aryloxycarbonyl and hetaryloxycarbonyl, wherein the alkoxycarbonyl, cycloalkyl, heterocycloalkyl, aryl, hetaryl, cycloalkoxy, heterocycloalkoxy, aryloxy, hetaryloxy, cycloalkoxycarbonyl, heterocycloalkoxycarbonyl, aryloxycarbonyl and hetaryloxycarbonyl are unsubstituted or comprise at least one radical selected from the group consisting of hydroxy, mercapto, $NE^1E^2$, $C(O)NE^1E^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl, and cycloalkyl, and $E^1$ and $E^2$ are each independently a radical selected from the group consisting of hydrogen, alkyl, cycloalkyl, and aryl, or $E^1$ and $E^2$ together with a nitrogen atom to which they are bound form a saturated nitrogen heterocyclyl which is unsubstituted or comprises an alkyl group as a substituent.

3. The process according to claim 1, wherein the terminal alkyne is acetylene.

4. The process according to claim 1, wherein the polydentate nitrogen ligand has formula IV:

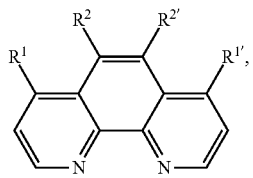

(IV)

wherein $R^1$, $R^{1'}$, $R^2$ and $R^{2'}$ are each independently selected from the group consisting of a hydrogen, hydroxy, mercapto, $NE^1E^2$, $C(O)NE^1E^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl, cycloalkyl, heterocycloalkyl, aryl, hetaryl, cycloalkoxy, heterocycloalkoxy, aryloxy, hetaryloxy, arylthio, hetarylthio, cycloalkoxycarbonyl, heterocycloalkoxycarbonyl, aryloxycarbonyl, and hetaryloxycarbonyl, the cycloalkyl, heterocycloalkyl, aryl, hetaryl, cycloalkoxy, heterocycloalkoxy, aryloxy, hetaryloxy, arylthio, hetarylthio, cycloalkoxycarbonyl, heterocycloalkoxycarbonyl, aryloxycarbonyl, and hetaryloxycarbonyl are unsubstituted or comprise at least one radical selected from the group consisting of hydroxy, mercapto, $NE^1E^2$, $C(O)NE^1E^2$, halogen, nitro, nitroso, formyl, alkyl, haloalkyl, alkoxy, haloalkoxy, alkylthio, haloalkylthio, alkylcarbonyl, alkylcarbonyloxy, alkylcarbonylthio, haloalkylcarbonyl, alkoxycarbonyl, cycloalkyl, heterocycloalkyl, aryl, hetaryl, cycloalkoxy, heterocycloalkoxy, aryloxy, hetaryloxy, cycloalkoxycarbonyl, heterocycloalkoxycarbonyl, aryloxycarbonyl, and hetaryloxycarbonyl, and $E^1$ and $E^2$ are each independently a radical selected from the group consisting of hydrogen, alkyl, cycloalkyl and aryl, or $E^1$ and $E^2$ together with a nitrogen atom to which they are bound form a saturated nitrogen heterocyclyl group which is unsubstituted or comprises an alkyl group as a substituent.

5. The process according to claim 4, wherein $R^1$ and $R^{1'}$ are a phenyl, optionally comprising 1 or 2 radicals, wherein the radical is at least one selected from the group consisting of halogen, alkyl, haloalkyl, alkoxy, and haloalkoxy.

6. The process according to claim 5, wherein the polydentate nitrogen ligand is 4,7-diphenyl-1,10-phenanthroline.

7. The process according to claim 1, wherein the ligand is a triarylphosphine.

8. The process according to claim 7, wherein the triarylphosphine is tri(p-fluorophenyl)phosphine.

9. The process according to claim 1, wherein the copper complex is a preformed copper complex.

10. The process according to claim 1, wherein the reacting comprises reacting in the presence of a catalyst, and
the amount of the catalyst is from 0.001 mol % to 20 mol % of Cu in the copper complex, based on the alkyne.

11. The process according to claim 1, wherein the solvent comprises at least one selected from the group consisting of an aliphatic hydrocarbon, an aromatic hydrocarbon, an amide, a urea, a nitrile, a sulfoxide, a sulfone, an alcohol, an ester, a carbonate, and an ether.

12. The process according to claim 1, wherein an acid corresponding to the base has a $pK_a$ in water at 25° C. of at least 3 pK units below a $pK_a$ of the alkyne.

13. The process according to claim 1, wherein the base is at least one selected from the group consisting of an alkali metal hydroxide, an alkaline earth metal hydroxide, an alkali metal carbonate, an alkaline earth metal carbonate, an alkali metal bicarbonate, an alkaline earth metal bicarbonate, an alkali metal oxide, an alkaline earth metal oxide, an alkali metal phosphate, an alkaline earth metal phosphate, an alkali metal hydrogenphosphate, an alkaline earth metal hydrogenphosphate, an alkali metal fluoride, an alkaline earth metal fluoride, an alkali metal carboxylate, and an alkaline earth metal carboxylate.

* * * * *